United States Patent
Molz, IV

(10) Patent No.: US 8,021,389 B2
(45) Date of Patent: Sep. 20, 2011

(54) SURGICAL STAPLE ASSEMBLY

(75) Inventor: Fred J. Molz, IV, Birmingham, AL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1526 days.

(21) Appl. No.: 11/435,943

(22) Filed: May 17, 2006

(65) Prior Publication Data

US 2007/0270906 A1 Nov. 22, 2007

(51) Int. Cl.
*A61B 17/08* (2006.01)

(52) U.S. Cl. ....... 606/219; 72/409.05; 72/469; 206/339; 206/340; 206/341; 606/75; 606/220

(58) Field of Classification Search .......... 606/138–139, 606/142, 75, 151, 219–220, 1; 227/83, 85, 227/90–91; 72/469, 409.05; 206/339–441
See application file for complete search history.

(56) References Cited

U.S. PATENT DOCUMENTS

| | | | | |
|---|---|---|---|---|
| 226,086 A * | 3/1880 | Lieb | | 227/71 |
| 2,329,849 A * | 9/1943 | Otis | | 72/469 |
| 2,817,839 A * | 12/1957 | Skrebba | | 227/128 |
| 3,713,533 A * | 1/1973 | Reimels | | 206/339 |
| 3,764,054 A * | 10/1973 | Monacelli | | 227/114 |
| 4,076,120 A * | 2/1978 | Carroll et al. | | 206/339 |
| 4,217,902 A * | 8/1980 | March | | 606/221 |
| 4,356,947 A * | 11/1982 | Marshall et al. | | 227/5 |
| 4,399,810 A * | 8/1983 | Samuels et al. | | 606/143 |
| 4,802,478 A * | 2/1989 | Powell | | 606/138 |
| 4,841,960 A | 6/1989 | Garner | | |
| 5,098,002 A * | 3/1992 | Hansch et al. | | 227/90 |
| 5,350,400 A * | 9/1994 | Esposito et al. | | 606/219 |
| 5,392,978 A * | 2/1995 | Velez et al. | | 227/177.1 |
| 6,322,580 B1 * | 11/2001 | Kanner | | 606/213 |
| 6,533,762 B2 * | 3/2003 | Kanner et al. | | 604/175 |
| 6,685,708 B2 | 2/2004 | Monassevitch et al. | | |
| 6,772,930 B2 * | 8/2004 | Ayres | | 227/83 |
| 6,773,437 B2 | 8/2004 | Ogilvie et al. | | |
| 7,473,258 B2 * | 1/2009 | Clauson et al. | | 606/139 |
| 7,621,433 B2 * | 11/2009 | Ivarsson | | 227/155 |
| 7,628,306 B2 * | 12/2009 | Spurchise et al. | | 227/175.1 |
| 2002/0019643 A1 * | 2/2002 | Gifford et al. | | 606/153 |
| 2002/0173793 A1 | 11/2002 | Allen | | |
| 2004/0084498 A1 * | 5/2004 | Ayres | | 227/83 |
| 2004/0262363 A1 * | 12/2004 | Elonsson et al. | | 227/76 |
| 2005/0043757 A1 | 2/2005 | Arad et al. | | |
| 2007/0210135 A1 * | 9/2007 | Ivarsson | | 227/134 |
| 2009/0254121 A1 * | 10/2009 | Newth et al. | | 606/219 |

FOREIGN PATENT DOCUMENTS

| EP | 0503271 | 9/1992 |
|---|---|---|
| EP | 0509513 | 10/1992 |
| WO | 0064365 | 11/2000 |

* cited by examiner

*Primary Examiner* — Darwin P Erezo
*Assistant Examiner* — Mark Mashack

(57) ABSTRACT

A surgical staple assembly is disclosed and can include a surgical staple. The surgical staple assembly can be moved between a first configuration and a second configuration. In the first configuration, the surgical staple can be in an original shape. Moreover, in the second configuration, the surgical staple can be in a deformed configuration.

29 Claims, 23 Drawing Sheets

SURGICAL STAPLE ASSEMBLY

FIELD OF THE DISCLOSURE

The present disclosure relates generally to surgical staples. More specifically, the present disclosure relates to devices for bending surgical staples made from shape memory metal alloys.

BACKGROUND

Surgical staples can be used to close surgical wounds and other wounds. Further, surgical staples can be used to treat certain spinal deformities, such as scoliosis. Some surgical staples can be made from shape memory metal alloys. A surgical staple made from a shape memory metal alloy can be deformed from an original shape and installed in a patient. Then, heat can be applied to the surgical staple to return the deformed staple to the original shape. When using multiple surgical staples, it may be desirable to bend the surgical staples to the same shape before installation in a patient.

DETAILED DESCRIPTION OF THE DRAWINGS

A surgical staple assembly is disclosed and can include a surgical staple. The surgical staple assembly can be moved between a first configuration and a second configuration. In the first configuration, the surgical staple can be in an original shape. Moreover, in the second configuration, the surgical staple can be in a deformed configuration.

In another embodiment, a surgical staple assembly is disclosed and can include a superior support plate and an inferior support plate that can be spaced from the superior support plate. The surgical staple assembly can also include a surgical staple that can be placed between the superior support plate and the inferior support plate. Further, the surgical staple assembly can be moved between a first configuration and a second configuration. In the first configuration, the surgical staple can be in an original shape. In the second configuration, the surgical staple can be in a deformed configuration.

In yet another embodiment, a method of treating a patient is disclosed and can include retrieving a surgical staple assembly that can have a surgical staple. The surgical staple assembly can be moved between a first configuration in which the surgical staple is in an original shape and a second configuration in which the surgical staple is deformed. The method can also include moving the surgical staple assembly to the second configuration.

In still another embodiment, a kit is disclosed and can include a plurality of surgical staple assemblies. Each surgical staple assembly can include a surgical staple. Further, each surgical staple assembly can bend each surgical staple to substantially the same shape. The kit can include different types and sizes of surgical staples. For example, the kit can include four-tine surgical staples, two-tine surgical staples, or a combination thereof.

Description of a Surgical Staple Assembly

Figure 1:
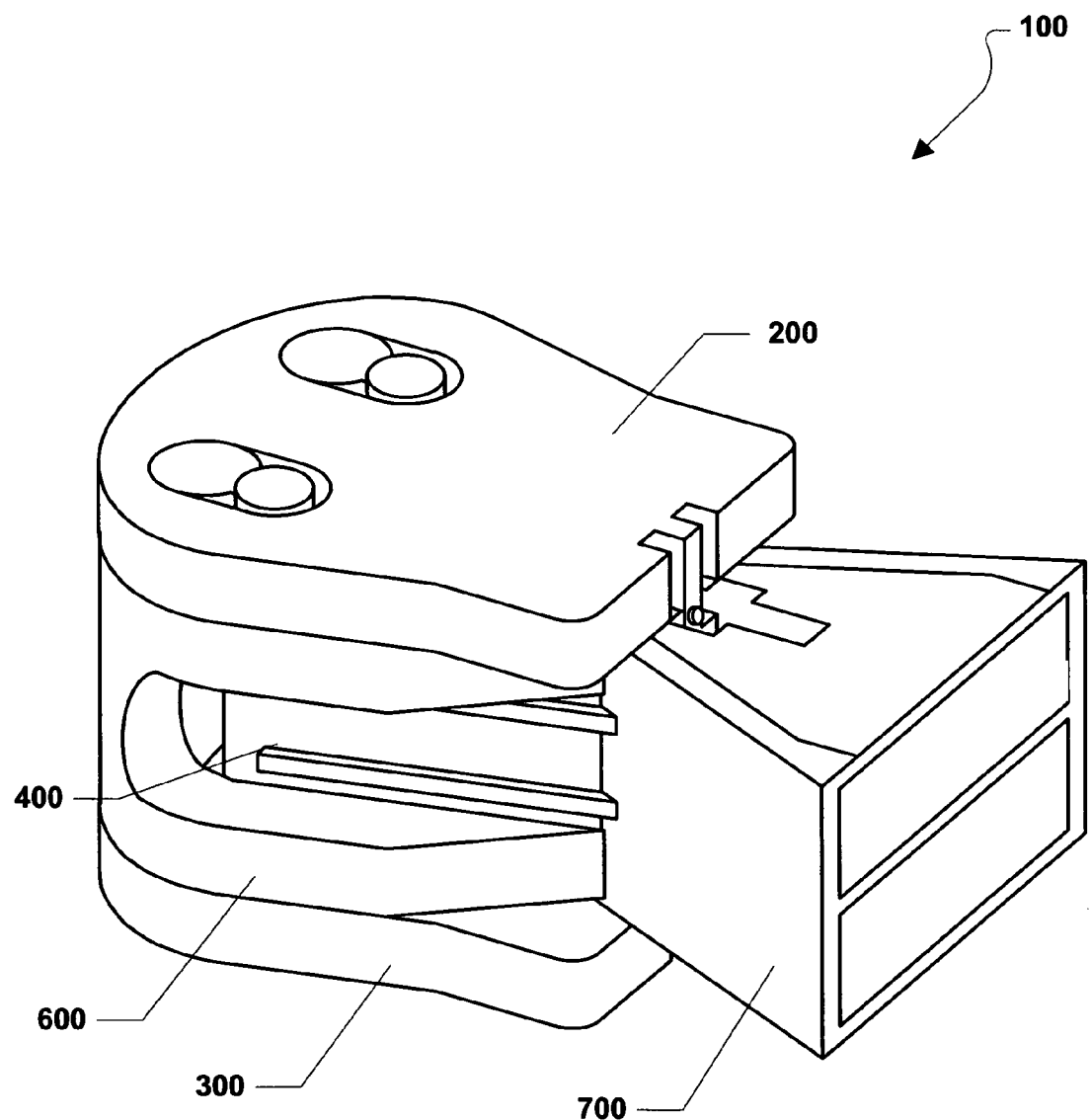
FIG. 1 is a perspective view of a surgical staple assembly.
Figure 2:
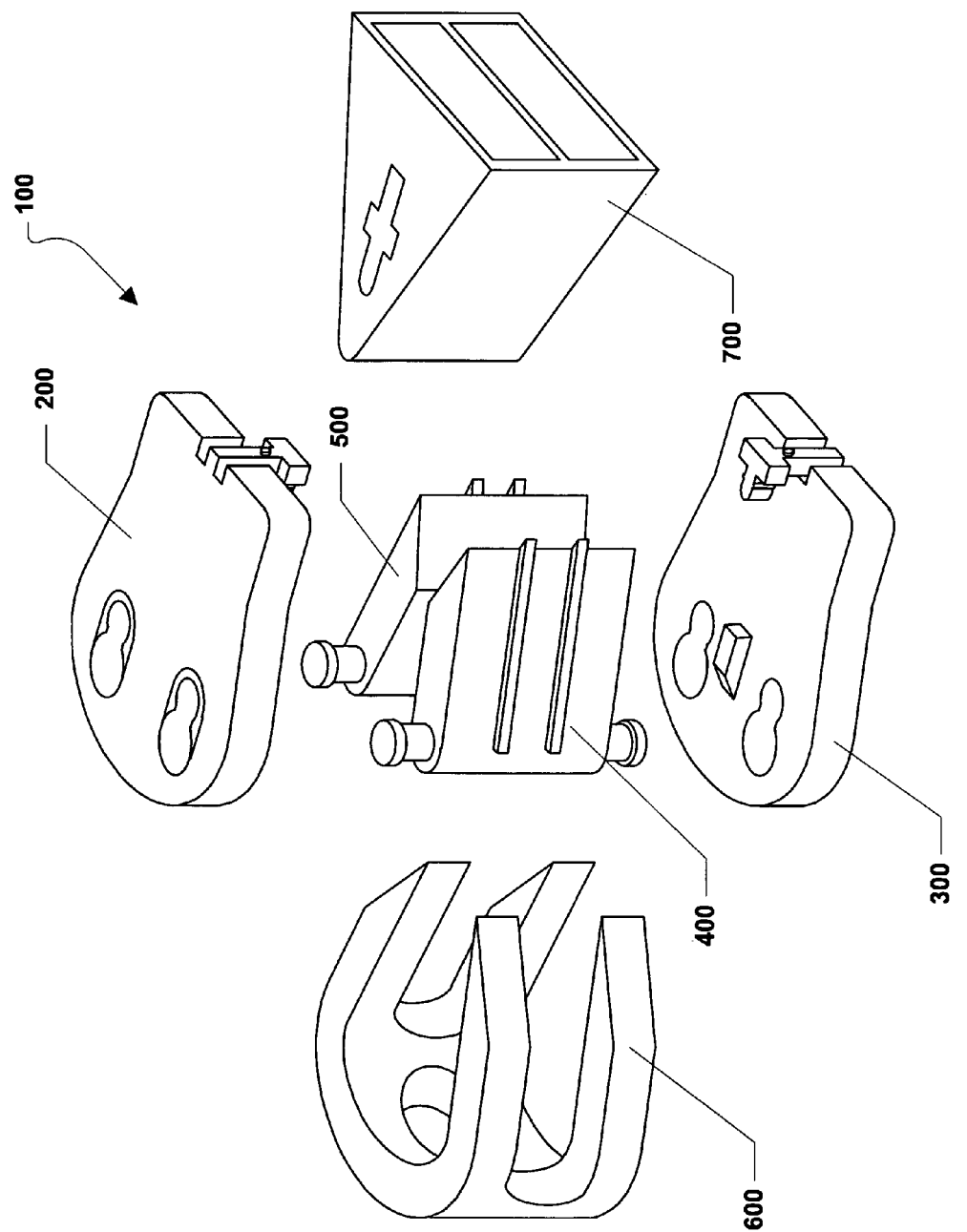
FIG. 2 is an exploded perspective view of the surgical staple assembly.

Referring initially to FIG. 1 and FIG. 2, a surgical staple assembly is shown and is generally designated 100. As illustrated in FIG. 1 and FIG. 2, the surgical staple assembly 100 can include a superior support plate 200 and an inferior support plate 300. In a particular embodiment, a first surgical staple bending arm 400 and a second surgical staple bending arm 500 can be installed between the support plates 200, 300. In certain embodiments, the bending arms 400, 500 can be rotably installed between the support plates 200, 300.

As shown in FIG. 1, a surgical staple 600 can be installed within the surgical staple assembly 100. In a particular embodiment, the surgical staple 600 can be installed between the support plates 200, 300 and around the bending arms 400, 500. During use of the surgical staple assembly 100, described in detail below, the bending arms 400, 500 can be used to bend the surgical staple 600 before the surgical staple 600 can be retrieved from the surgical staple assembly 100.

FIG. 1 further shows that the surgical staple assembly 100 can include a bending wedge 700. In a particular embodiment, the bending wedge 700, e.g., a portion of the bending wedge 700, can be placed between the first bending arm 400 and the second bending arm 500 within the support plates 200, 300. As described in greater detail below, the bending wedge 700 can be moved into the surgical staple assembly 100 in order to move the bending arms 400, 500 outward relative to the surgical staple assembly 100. As the bending arms 400, 500 move outward, the surgical staple 600 can be deformed. Further, the surgical staple 600 can be removed from the surgical staple assembly 100 after the deformation action is complete.

In a particular embodiment, the support plates 200, 300, the bending arms 400, 500, and the bending wedge 700 can be made from one or more rigid materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, polyimide materials, or a combination thereof. Further, the polyolefin materials can include polypropylene, polyethylene, halogenated polyolefin, flouropolyolefin, or a combination thereof. The polyaryletherketone (PAEK) materials can include polyetherketone (PEK), polyetheretherketone (PEEK), polyetherketoneketone (PEKK), polyetherketoneetherketoneketone (PEKEKK), or a combination thereof. Alternatively, the support plates 200, 300, the bending arms 400, 500, and the bending wedge 700 can be made from any other substantially rigid materials.

Further, in a particular embodiment, the surgical staple 600 can be made from a biocompatible, shape memory metal alloy. For example, the surgical staple 600 can be made from a shape memory metal alloy of titanium and nickel, e.g., nitinol. Alternatively, the surgical staple 60 can be made from a biocompatible, shape memory polymer.

In a particular embodiment, the components of the surgical staple assembly 100 can be manufactured using a machining process, a forging process, a forming process, an injection molding process, a metal injection molding process, or a combination thereof. Alternatively, the components of the surgical staple assembly can be manufactured using another process well known in the art.

Description of the Support Plates

Figure 3:
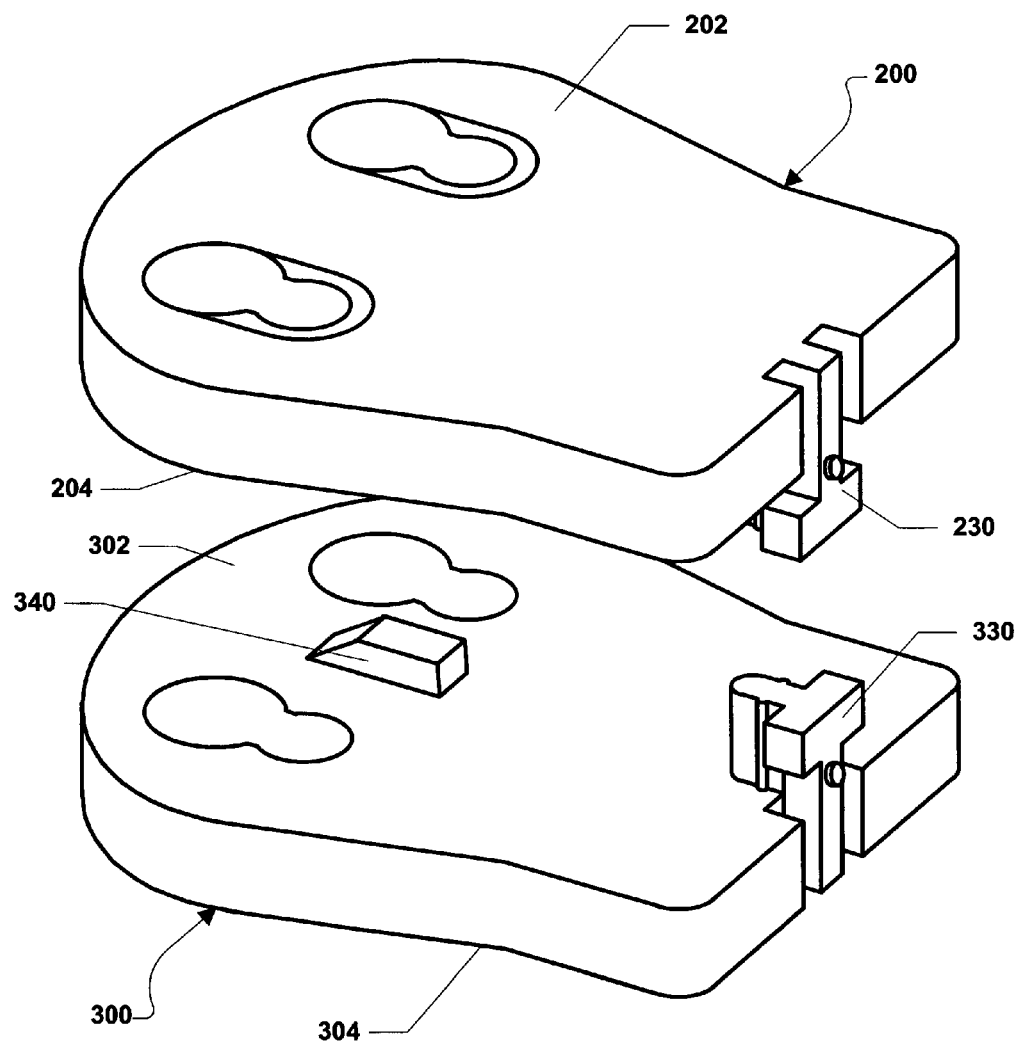
FIG. 3 is a perspective view of a superior support plate and an inferior support plate of the surgical staple assembly.
Figure 4:
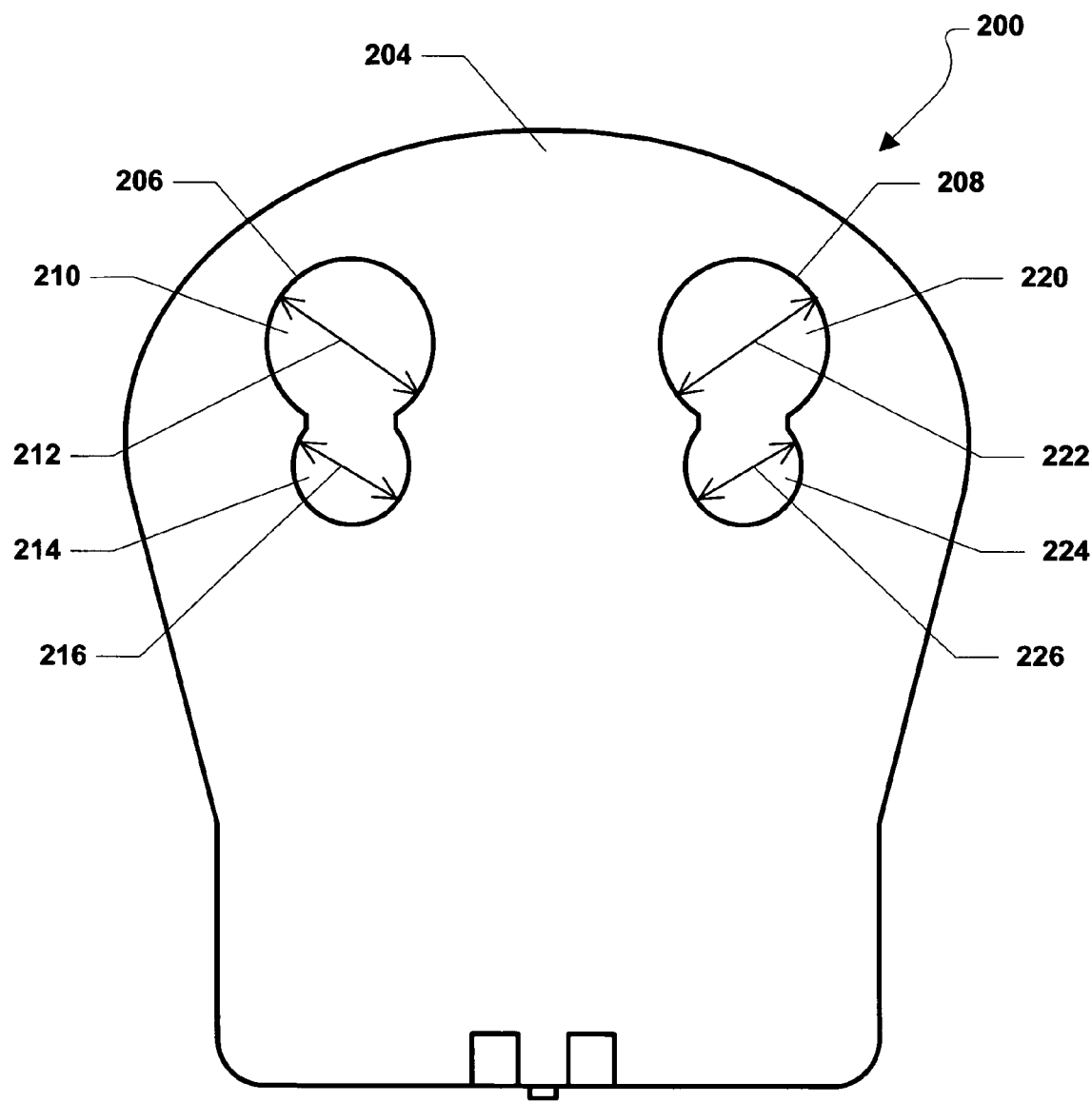
FIG. 4 is a top plan view of the superior support plate.
Figure 5:
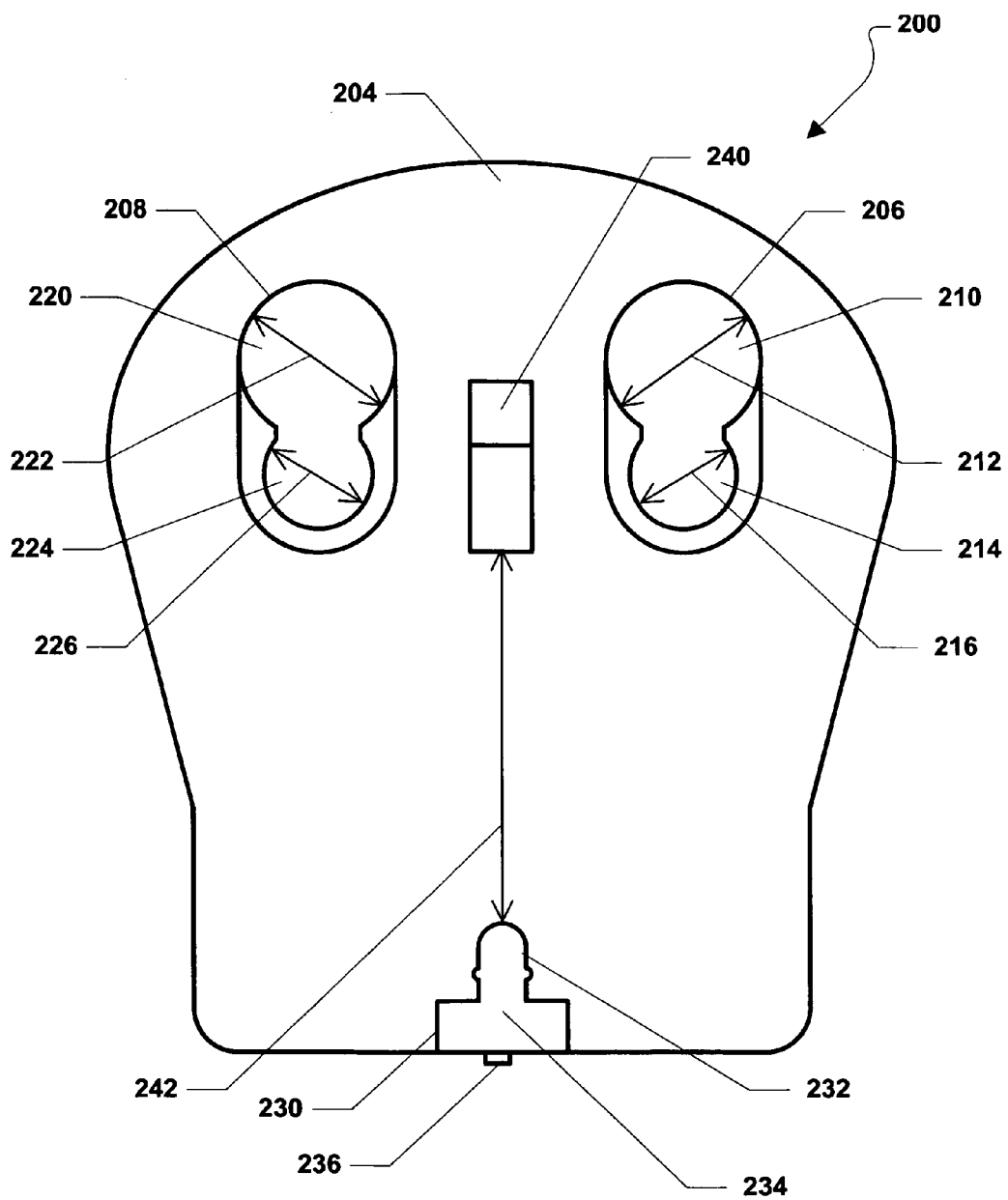
FIG. 5 is a bottom plan view of the superior support plate.

Referring now to FIG. 3 through FIG. 7, details concerning the support plates 200, 300 can be seen. As shown in FIG. 3 through FIG. 5, the superior support plate 200 includes a superior surface 202 and an inferior surface 204. Further, the superior support plate 200 can include a first hole 206 and a second hole 208 therethrough. The first hole 206 can include a first portion 210 having a first diameter 212. Also, the first hole 206 can include a second portion 214 having a second diameter 216. In a particular embodiment, the first diameter 212 can be greater than the second diameter 216.

FIG. 4 and FIG. 5 also show that the second hole 208 can include a first portion 220 having a first diameter 222 and a second portion 224 having a second diameter 226. In a particular embodiment, the first diameter 222 can be greater than the second diameter 226. Each of the holes 206, 208 is configured to receive and engage a post from a bending arm, described in detail below. For example, a post can be inserted through the larger, first portion 210, 220 of a hole 206, 208 and then, moved linearly into the smaller, second portion 214, 224 of the hole 206, 208. As the post is moved into the smaller, second portion 214, 224 of the hole 206, 208, the post can snap into place within the smaller, second portion 214, 224 of the hole 206, 208.

As shown in FIG. 3 and FIG. 5, a superior bending wedge guide 230 can extend from the superior support plate 200, e.g., through the inferior surface 204 of the superior support plate 200. The superior bending wedge guide 230 can include a post 232 and a cap 234. In a particular embodiment, the post 232 can extend substantially perpendicular from the inferior surface 204 of the superior support plate 200. Further, in a particular embodiment, the cap 234 of the superior bending wedge guide 230 can be generally T-shaped. As described in greater detail below, the superior bending wedge guide 230 can be configured to receive and engage the bending wedge 700. Further, the superior bending wedge guide 230 can allow the bending wedge 700 to slide relative to the superior support plate 200.

The superior bending wedge guide 230 can also include a protrusion 238 extending therefrom. The protrusion 238 can be part of an audible clicking mechanism, e.g., a clicking mechanism similar to a dog training clicker, which can be incorporated in the superior bending wedge guide 230. Accordingly, during operation of the surgical staple assembly 100, described herein, the protrusion 238 can be contacted by the bending wedge 700. Further, when the button 238 is contacted, a clicking noise can be generated. The clicking noise can serve as a signal to a surgeon that a surgical staple 600 within the surgical staple assembly 100 is fully deformed, or deployed.

FIG. 3 and FIG. 5 also show that a superior bending wedge stop 240 can extend from the inferior surface 204 of the superior support plate 200. The superior bending wedge stop 240 can prevent the bending wedge 700 from sliding relative to the superior support plate 200 beyond the superior bending wedge stop 240. More specifically, the bending wedge 700 can slide relative to the superior support plate 200 between the superior bending wedge guide 230 and the superior bending wedge stop 240, e.g., along line 242.

Figure 6:
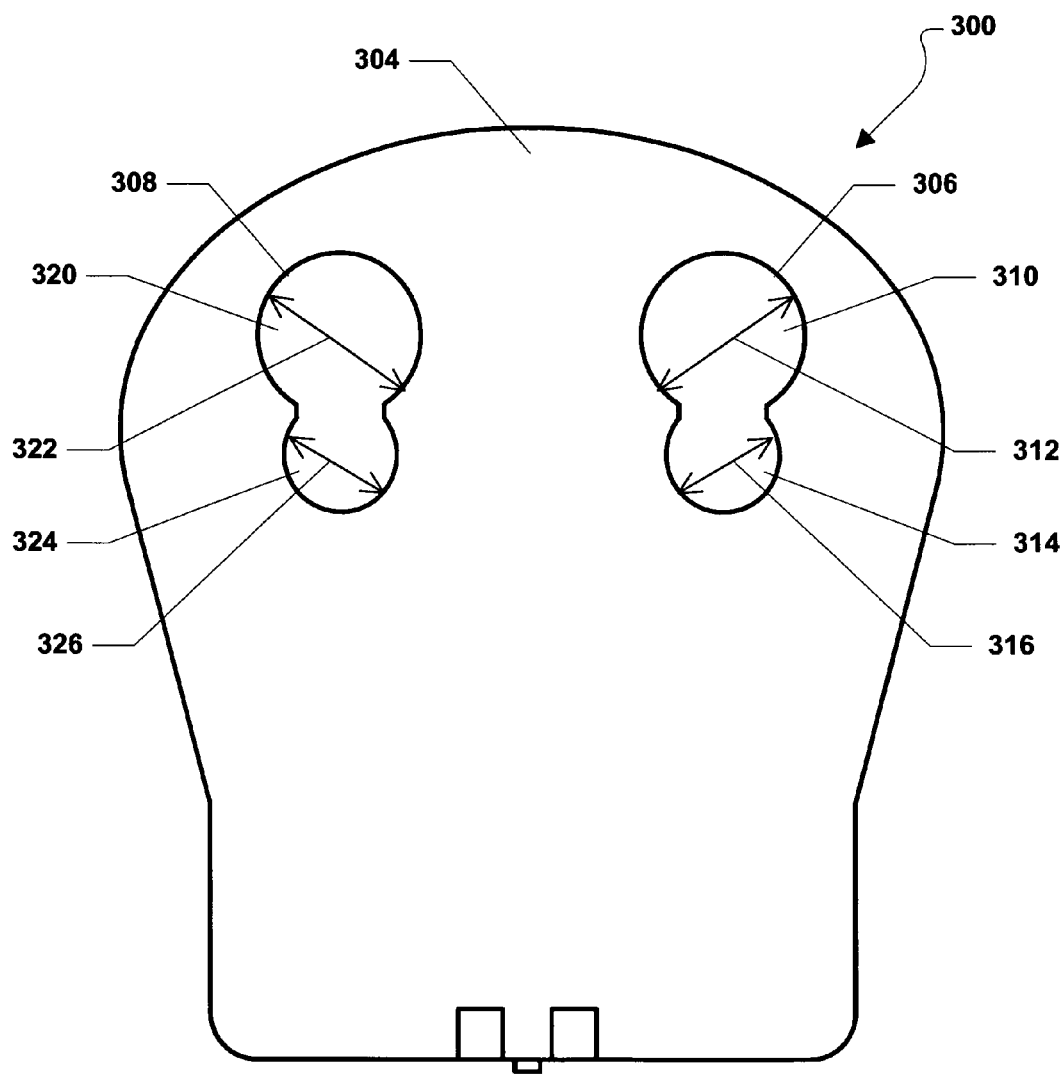
FIG. 6 is a bottom plan view of the inferior support plate.
Figure 7:
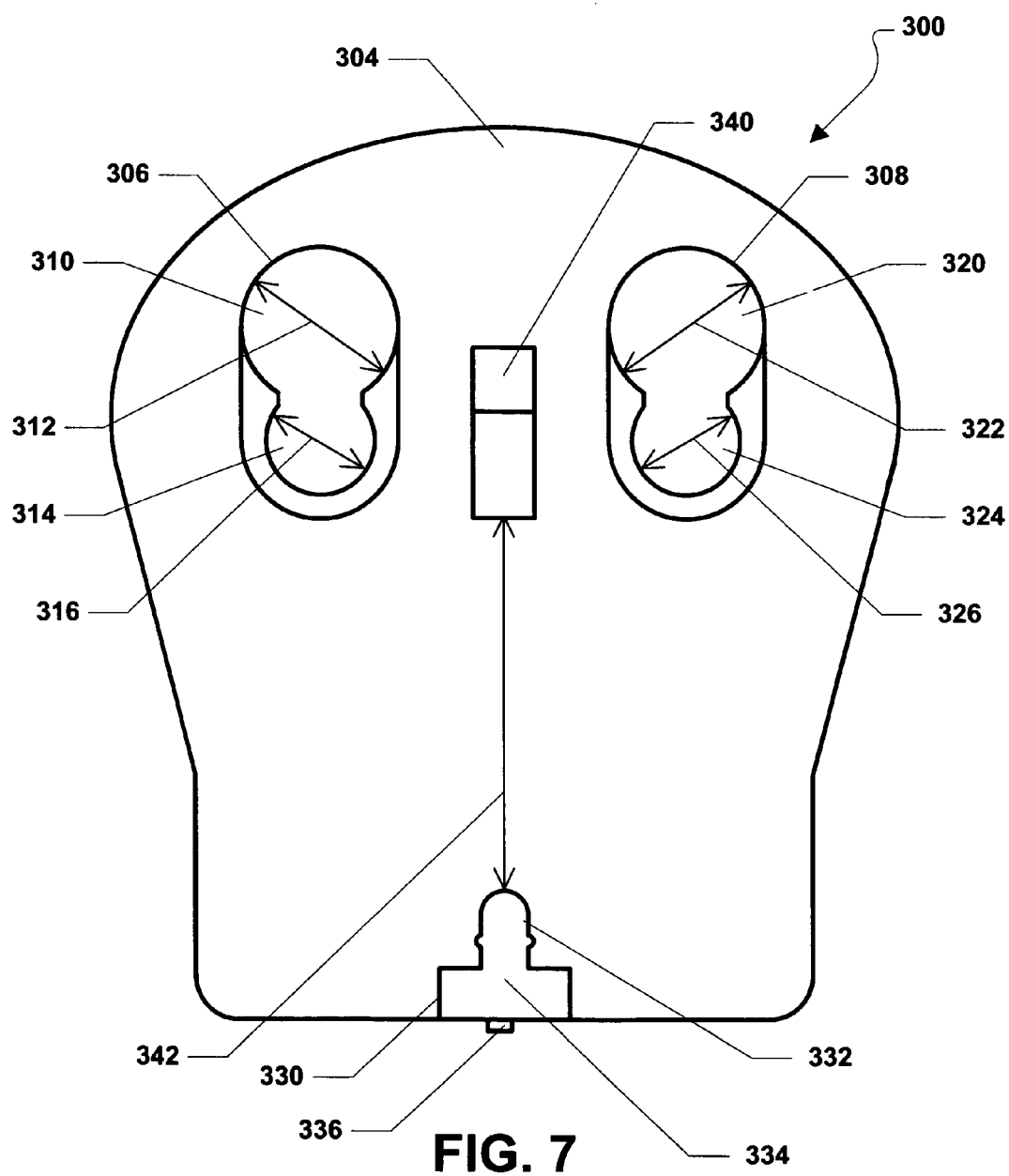
FIG. 7 is a top plan view of the inferior support plate.

As shown in FIG. 3, FIG. 6 and FIG. 7, the inferior support plate 300 includes a superior surface 302 and an inferior surface 304. Further, the inferior support plate 300 can include a first hole 306 and a second hole 308 therethrough. The first hole 306 can include a first portion 310 having a first diameter 312. Also, the first hole 306 can include a second portion 314 having a second diameter 316. In a particular embodiment, the first diameter 312 can be greater than the second diameter 316.

FIG. 6 and FIG. 7 also show that the second hole 308 can include a first portion 320 having a first diameter 322 and a second portion 324 having a second diameter 326. In a particular embodiment, the first diameter 322 can be greater than the second diameter 326. Each of the holes 306, 308 is configured to receive and engage a post from a bending arm, described in detail below. For example, a post can be inserted through the larger, first portion 310, 320 of a hole 306, 308 and then, moved linearly into the smaller, second portion 314, 324 of the hole 306, 308. As the post is moved into the smaller, second portion 314, 324 of the hole 306, 308, the post can snap into place within the smaller, second portion 314, 324 of the hole 306, 308.

As shown in FIG. 3 and FIG. 7, an inferior bending wedge guide 330 can extend from the inferior support plate 300, e.g., through the superior surface 304 of the inferior support plate 300. The inferior bending wedge guide 330 can include a post 332 and a cap 334. In a particular embodiment, the post 332 can extend substantially perpendicular from the superior surface 304 of the inferior support plate 300. Further, in a particular embodiment, the cap 334 of the inferior bending wedge guide 330 can be generally T-shaped. As described in greater detail below, the inferior bending wedge guide 330 can be configured to receive and engage the bending wedge 700. Further, the inferior bending wedge guide 330 can allow the bending wedge 700 to slide relative to the inferior support plate 300.

The inferior bending wedge guide 330 can also include a protrusion 338 extending therefrom. The protrusion 338 can be part of an audible clicking mechanism, e.g., a clicking mechanism similar to a dog training clicker, which can be incorporated in the inferior bending wedge guide 330. Accordingly, during operation of the surgical staple assembly 100, described herein, the protrusion 338 can be contacted by the bending wedge 700. Further, when the protrusion 338 is contacted, a clicking noise can be generated. The clicking noise can serve as a signal to a surgeon that a surgical staple 600 within the surgical staple assembly 100 is fully deformed, or deployed.

FIG. 3 and FIG. 5 also show that an inferior bending wedge stop 340 can extend from the superior surface 304 of the support plate 300. The inferior bending wedge stop 340 can prevent the bending wedge 700 from sliding relative to the inferior support plate 300 beyond the inferior bending wedge stop 340. More specifically, the bending wedge 700 can slide relative to the inferior support plate 300 between the inferior bending wedge guide 330 and the inferior bending wedge stop 340, e.g., along line 342.

Description of the Bending Arms

Figure 8:
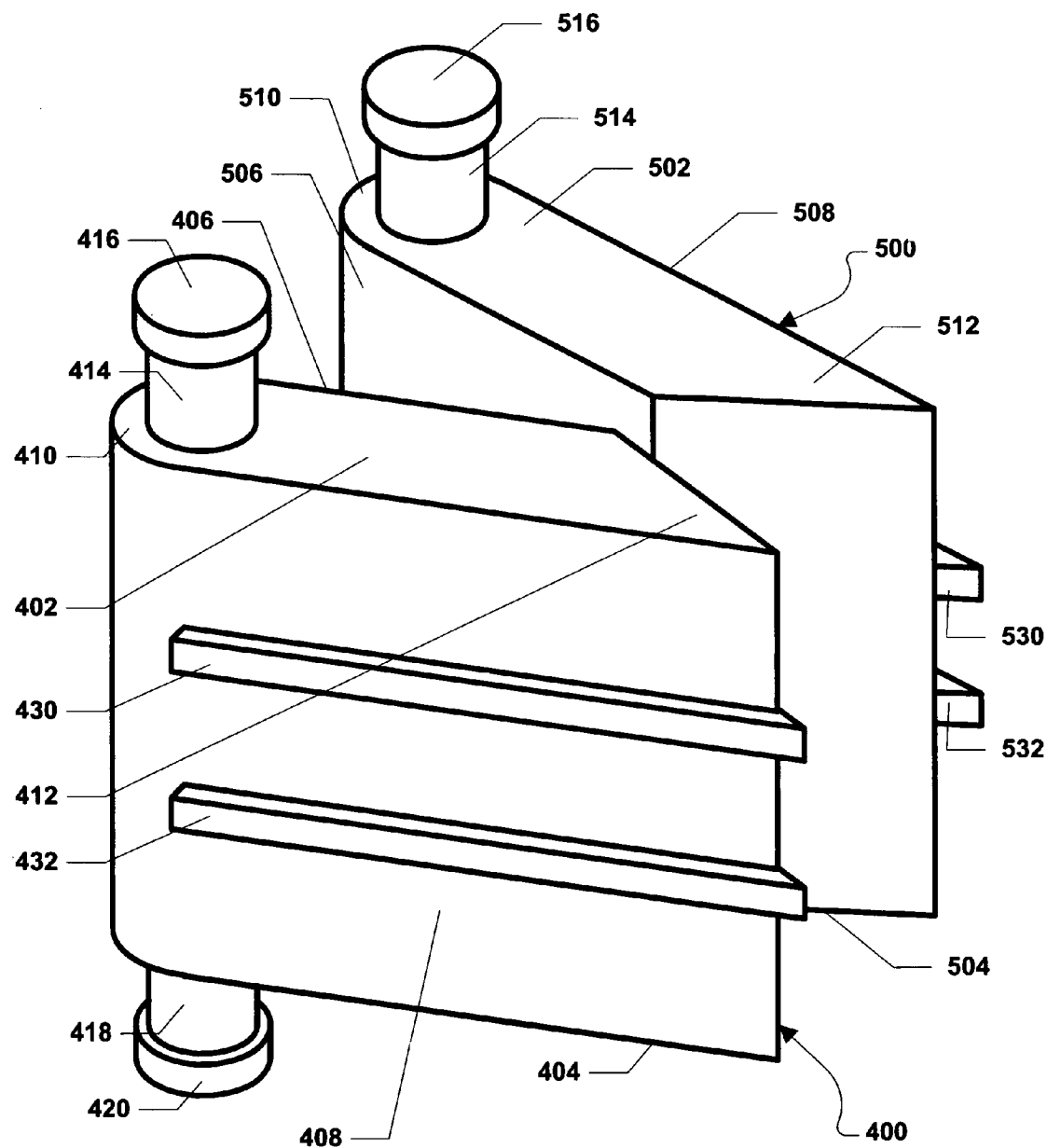
FIG. 8 is a perspective view of a first surgical staple bending plate and a second surgical staple bending plate of the surgical staple assembly.
Figure 9:
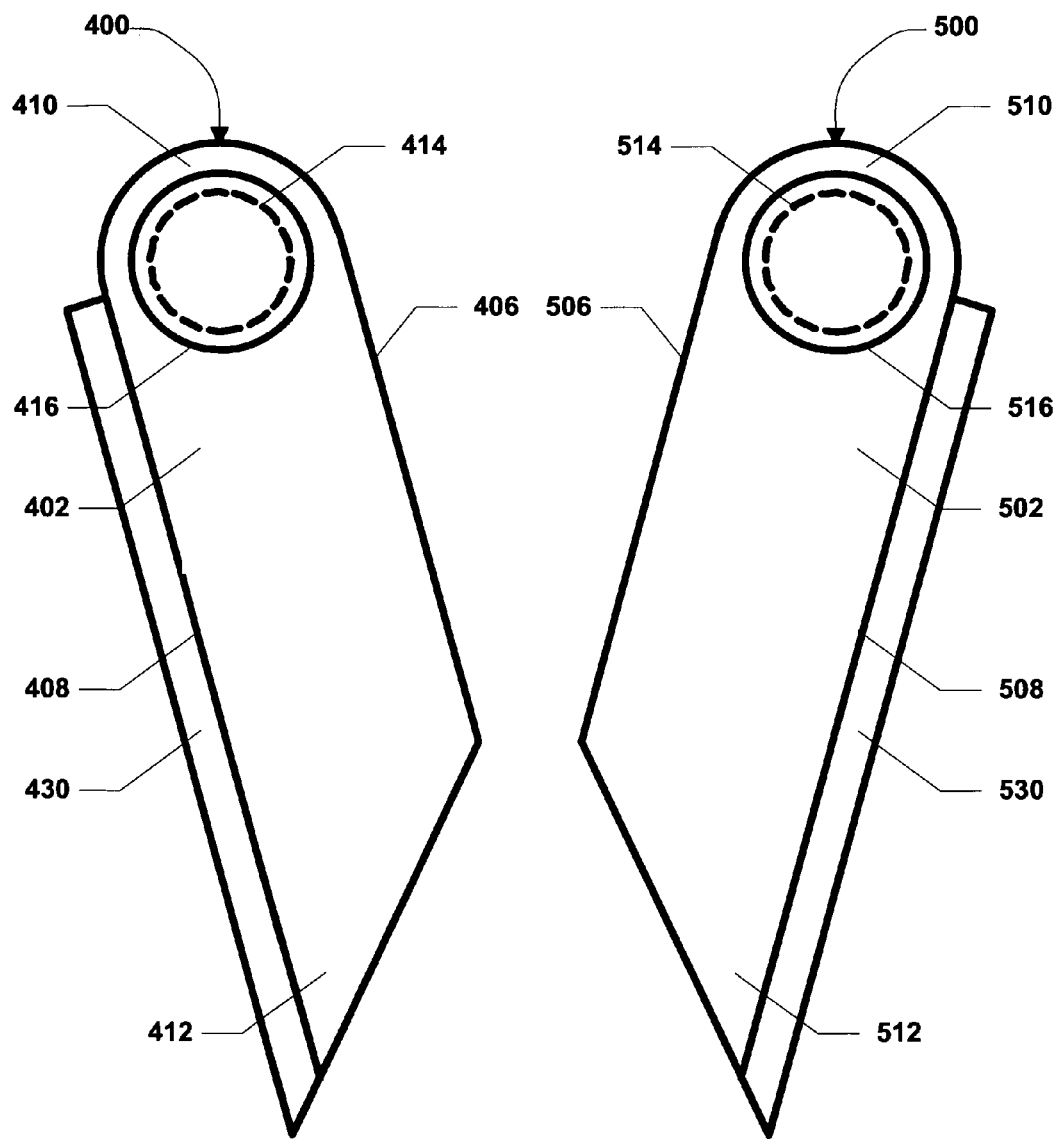
FIG. 9 is top plan view of the first surgical staple bending plate and the second surgical staple bending plate.
Figure 10:
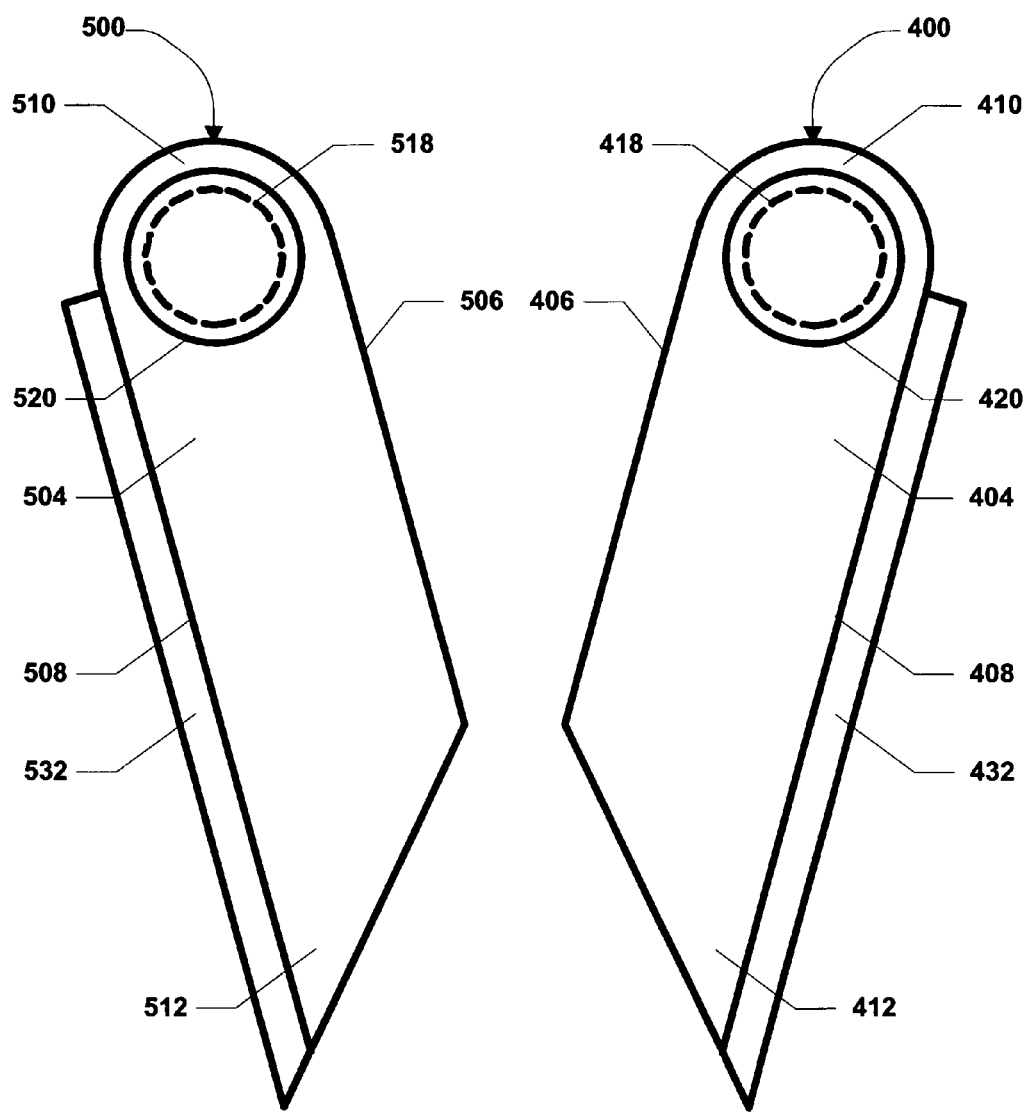
FIG. 10 is a bottom plan view of the first surgical staple bending plate and the second surgical staple bending plate.

Referring to FIG. 8 through FIG. 10, details concerning the configuration of the bending arms 400, 500 are shown. As illustrated in FIG. 8 through FIG. 10, the first bending arm 400 can include a superior surface 402 and an inferior surface 404. In a particular embodiment, the inferior surface 404 is substantially parallel to the superior surface 402. FIG. 8 through FIG. 10 show that the first bending arm 400 can also include an inner surface 406 and an outer surface 408. In a particular embodiment, the outer surface 408 is substantially parallel to the inner surface 406. Further, the inner surface 406 and the outer surface 408 are substantially perpendicular to the superior surface 402 and the inferior surface 404.

As illustrated in FIG. 9 and FIG. 10, the first bending arm 400 can include a proximal end 410 and a distal end 412. A superior post 414 can extend from the superior surface 402 of the first bending arm 400 near the distal end 410 of the first bending arm 400. In a particular embodiment, the superior post 414 can extend substantially perpendicular from the superior surface 402. Also, the superior post 414 can include a superior end cap 416.

An inferior post 418 can extend from the inferior surface 402 of the first bending arm 400 near the distal end 410 of the first bending arm 400. In a particular embodiment, the inferior post 418 can extend substantially perpendicular from the inferior surface 404. Moreover, the inferior post 418 can be substantially co-linear and aligned with the superior post 414. The inferior post 418 can also include an inferior end cap 420.

In a particular embodiment, the superior post 414 of the first bending arm 400 can engage the first hole 206 in the superior support plate 200 (FIG. 5). More specifically, the superior post 414 can be inserted through the larger, first portion 210 of the first hole 206 and snapped into the smaller, second portion 214 of the first hole 206. The superior post 414 can rotate within the smaller, second portion 214 of the first hole 206. Also, the superior end cap 416 can substantially prevent the superior support plate 200 from becoming disengaged with the superior post 414.

Also, in a particular embodiment, the inferior post 418 of the first bending arm 400 can engage the first hole 306 in the inferior support plate 300 (FIG. 6). More specifically, the inferior post 418 can be inserted through the larger, first portion 310 of the first hole 306 and snapped into the smaller, second portion 314 of the first hole 306. The inferior post 418 can rotate within the smaller, second portion 314 of the first hole 306. Further, the inferior end cap 420 can substantially prevent the inferior support plate 300 from becoming disengaged with the inferior post 418.

FIG. 9 and FIG. 10 show that that the inner surface 406 of the first bending arm 400 can be shorter than the outer surface 408 of the first bending arm 400. As such, the distal end 412 of the first bending arm 400 can be angled or tapered from the outer surface 408 to the inner surface 406. In a particular embodiment, when the surgical staple assembly 100 is assembled, as shown in FIG. 1, the bending wedge 700 can engage the angled distal end 412 of the first bending arm 400. Further, as the bending wedge 700 is slid into the surgical staple assembly 100, the bending wedge 700 can apply an outward force to the first bending arm 400 and the bending wedge can cause the first bending arm 400 to rotate outward around the posts 414, 418.

The first bending arm 400 can also include a superior rib 430 and an inferior rib 432. As shown, the superior rib 430 and the inferior rib 432 can extend from the outer surface 408 of the first bending arm 400. In a particular embodiment, the ribs 430, 432 are substantially parallel to each other, the superior surface 402, and the inferior surface 404. Further, the ribs 430, 432 can be spaced from each other a distance that corresponds to a width of a two-tine staple, described below. As such, a two-tine staple can be assembled with the surgical staple assembly 100 in lieu of the four-tine staple 600, described herein. In particular, the two-tine staple can be slid between the ribs 430, 432 and the ribs 430, 432 can maintain the two-tine staple near a center of the first bending arm 400.

As illustrated in FIG. 8 through FIG. 10, the second bending arm 500 can include a superior surface 502 and an inferior surface 504. In a particular embodiment, the inferior surface 504 is substantially parallel to the superior surface 502. FIG. 8 through FIG. 10 show that the second bending arm 500 can also include an inner surface 506 and an outer surface 508. In a particular embodiment, the outer surface 508 is substantially parallel to the inner surface 506. Further, the inner surface 506 and the outer surface 508 are substantially perpendicular to the superior surface 502 and the inferior surface 504.

As illustrated in FIG. 9 and FIG. 10, the second bending arm 500 can include a proximal end 510 and a distal end 512. A superior post 514 can extend from the superior surface 502 of the second bending arm 500 near the proximal end 510 of the second bending arm 500. In a particular embodiment, the superior post 514 can extend substantially perpendicular from the superior surface 502. Also, the superior post 514 can include a superior end cap 516.

An inferior post 518 can extend from the inferior surface 502 of the second bending arm 500 near the proximal end 510 of the second bending arm 500. In a particular embodiment, the inferior post 518 can extend substantially perpendicular from the inferior surface 504. Moreover, the inferior post 518 can be substantially co-linear and aligned with the superior post 514. The inferior post 518 can also include an inferior end cap 520.

In a particular embodiment, the superior post 514 of the second bending arm 500 can engage the second hole 208 in the superior support plate 200 (FIG. 5). More specifically, the superior post 514 can be inserted through the larger, first portion 220 of the second hole 208 and snapped into the smaller, second portion 224 of the second hole 208. The superior post 514 can rotate within the smaller, second portion 224 of the second hole 208. Also, the superior end cap 516 can substantially prevent the superior support plate 200 from becoming disengaged with the superior post 514.

Also, in a particular embodiment, the inferior post 518 of the second bending arm 500 can engage the second hole 308 in the inferior support plate 300 (FIG. 6). More specifically, the inferior post 518 can be inserted through the larger, first portion 320 of the second hole 308 and snapped into the smaller, second portion 324 of the second hole 308. The inferior post 518 can rotate within the smaller, second portion 324 of the second hole 306. Further, the inferior end cap 520 can substantially prevent the inferior support plate 300 from becoming disengaged with the inferior post 518.

FIG. 9 and FIG. 10 show that that the inner surface 506 of the second bending arm 500 can be shorter than the outer surface 508 of the second bending arm 500. As such, the distal end 512 of the second bending arm 500 can be angled or tapered from the outer surface 508 to the inner surface 506. In a particular embodiment, when the surgical staple assembly 100 is assembled, as shown in FIG. 1, the bending wedge 700 can engage the angled distal end 512 of the second bending arm 500. Further, as the bending wedge 700 is slid into the surgical staple assembly 100, the bending wedge 700 can apply an outward force to the second bending arm 500 and the bending wedge can cause the second bending arm 500 to rotate outward around the posts 514, 518.

The second bending arm 500 can also include a superior rib 530 and an inferior rib 532. As shown, the superior rib 530 and the inferior rib 532 can extend from the outer surface 508 of the second bending arm 500. In a particular embodiment, the ribs 530, 532 are substantially parallel to each other, the superior surface 502, and the inferior surface 504. Further, the ribs 530, 532 can be spaced from each other a distance that corresponds to a width of a two-tine staple, described below. As such, a two-tine staple can be assembled with the surgical staple assembly 100 in lieu of the four-tine staple 600, described herein. In particular, the two-tine staple can be slid between the ribs 530, 532 and the ribs 530, 532 can maintain the two-tine staple near a center of the second bending arm 500.

Description of the Surgical Staple

Figure 11:
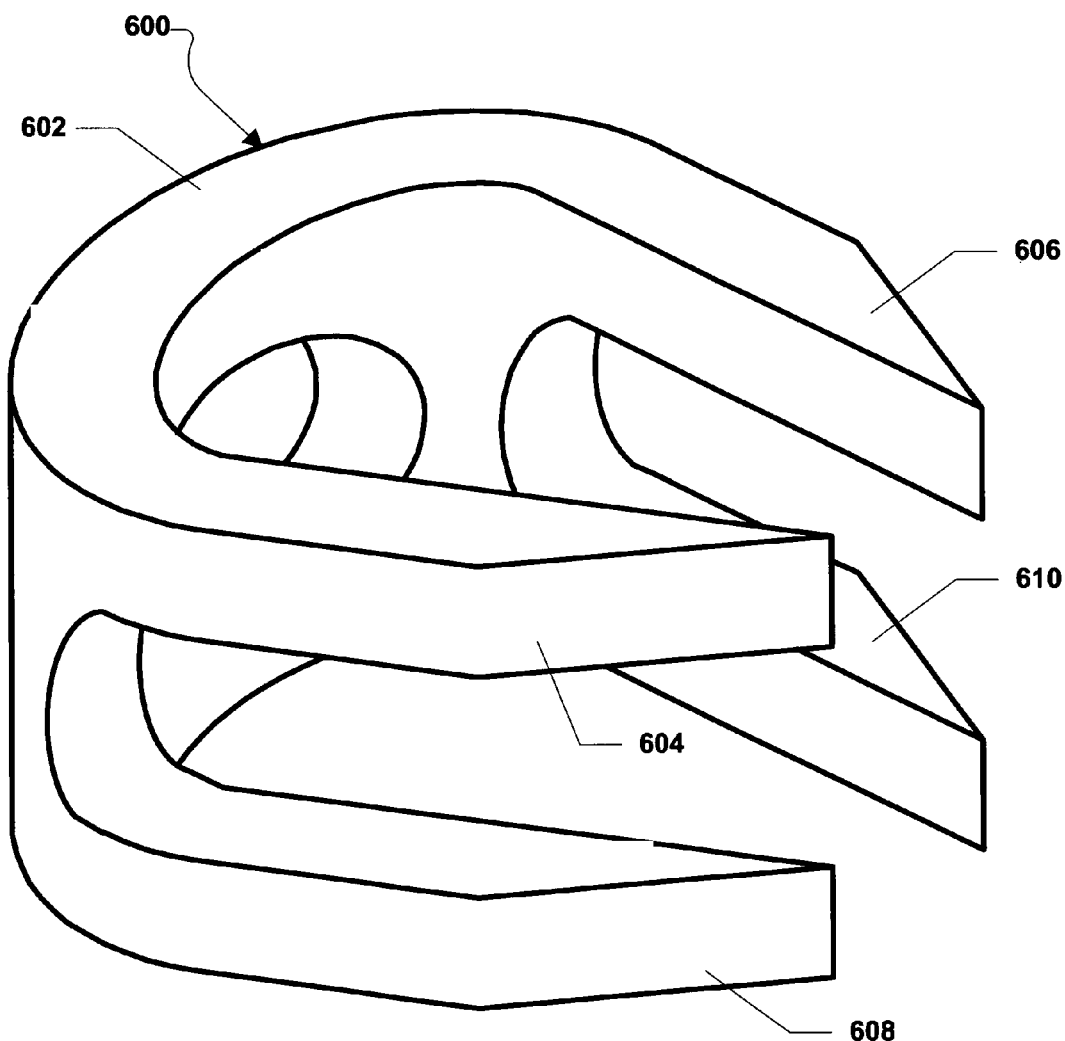
FIG. 11 is a perspective view of a surgical staple of the surgical staple assembly.
Figure 12:
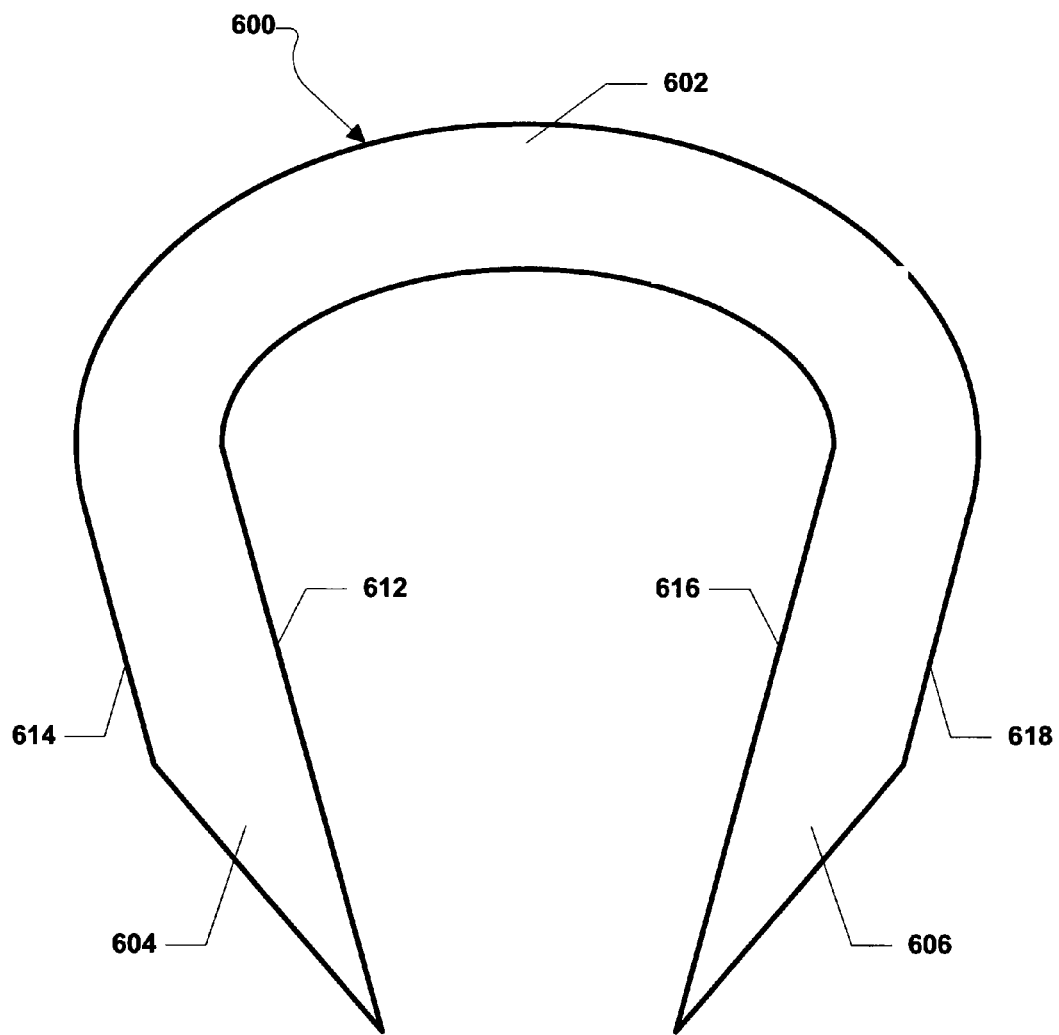
FIG. 12 is a top plan view of the surgical staple.
Figure 13:
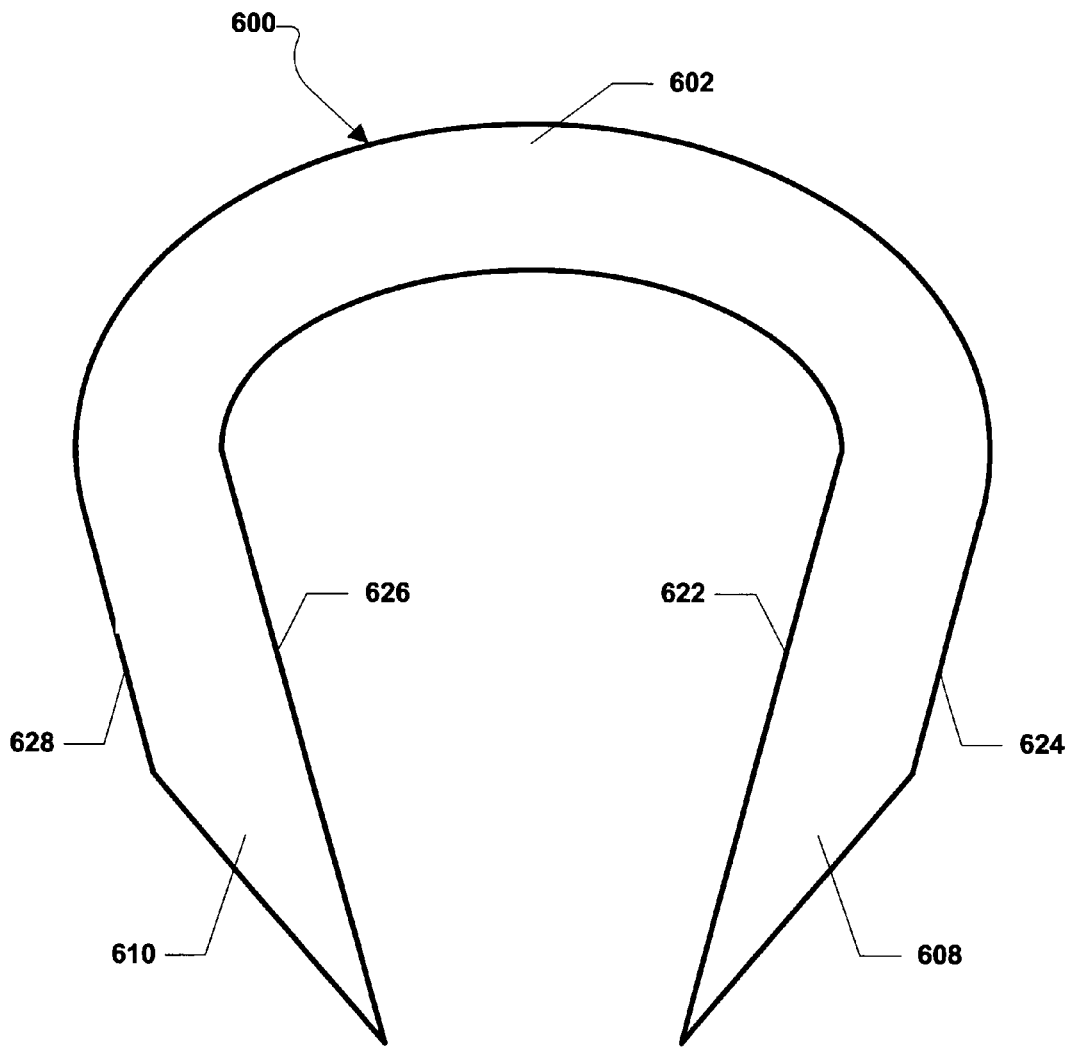
FIG. 13 is a bottom plan view of the surgical staple.

Referring to FIG. 11 through 13, details regarding the surgical staple 600 are shown. As shown, the surgical staple 600 can include a base 602. A first superior tine 604 and a second superior tine 606 can extend from the base 602. Further, a first inferior tine 608 and a second inferior tine 610 can extend from the base 602. In a particular embodiment, the first superior tine 604 can be substantially parallel to the first inferior tine 608. Also, the second superior tine 606 can be substantially parallel to the second inferior tine 610.

As shown in FIG. 12, the first superior tine 604 can include an inner surface 612 and an outer surface 614. The second superior tine 606 can also include an inner surface 616 and an outer surface 618. FIG. 13 indicates that the first inferior tine 608 can include an inner surface 622 and an outer surface 624. Further, the second inferior tine 610 can include an inner surface 626 and an outer surface 628.

When the surgical staple assembly 100 is assembled, as illustrated in FIG. 1, the surgical staple 600 can be disposed around the bending arms 400, 500. Specifically, the inner surface 612 of the first superior tine 604 and the inner surface 622 of the first inferior tine 608 can be adjacent to the outer surface 408 of the first bending arm 400. Also, the inner surface 616 of the second superior tine 606 and the inner surface 626 of the second inferior tine 610 can be adjacent to the outer surface 508 of the second bending arm 400.

Accordingly, as the bending arms 400, 500 are pushed outward by the bending wedge 700, the bending arms 400, 500 can bend the tines 604, 606, 608, 610 of the surgical staple 600. More specifically, as the first bending arm 400 is pushed outward, the first bending arm 400 can bend the first superior tine 604 and the first inferior tine 608 of the surgical staple 600. Moreover, as the second bending arm 500 is pushed outward, the second bending arm 500 can bend the second superior tine 606 and the second inferior tine 610 of the surgical staple 600.

Description of the Bending Wedge

Figure 14:
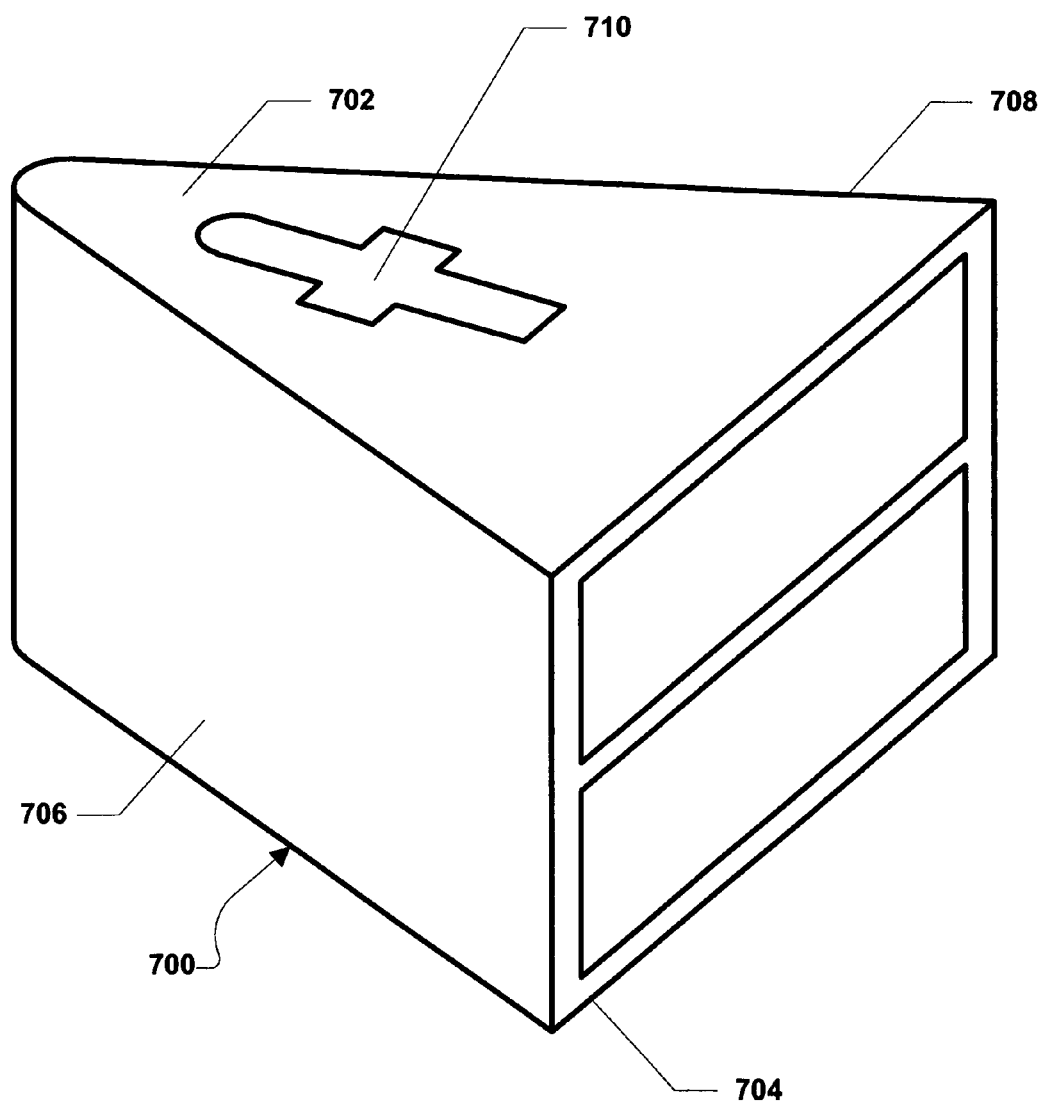
FIG. 14 is a perspective view of a bending wedge of the surgical staple assembly.
Figure 15:
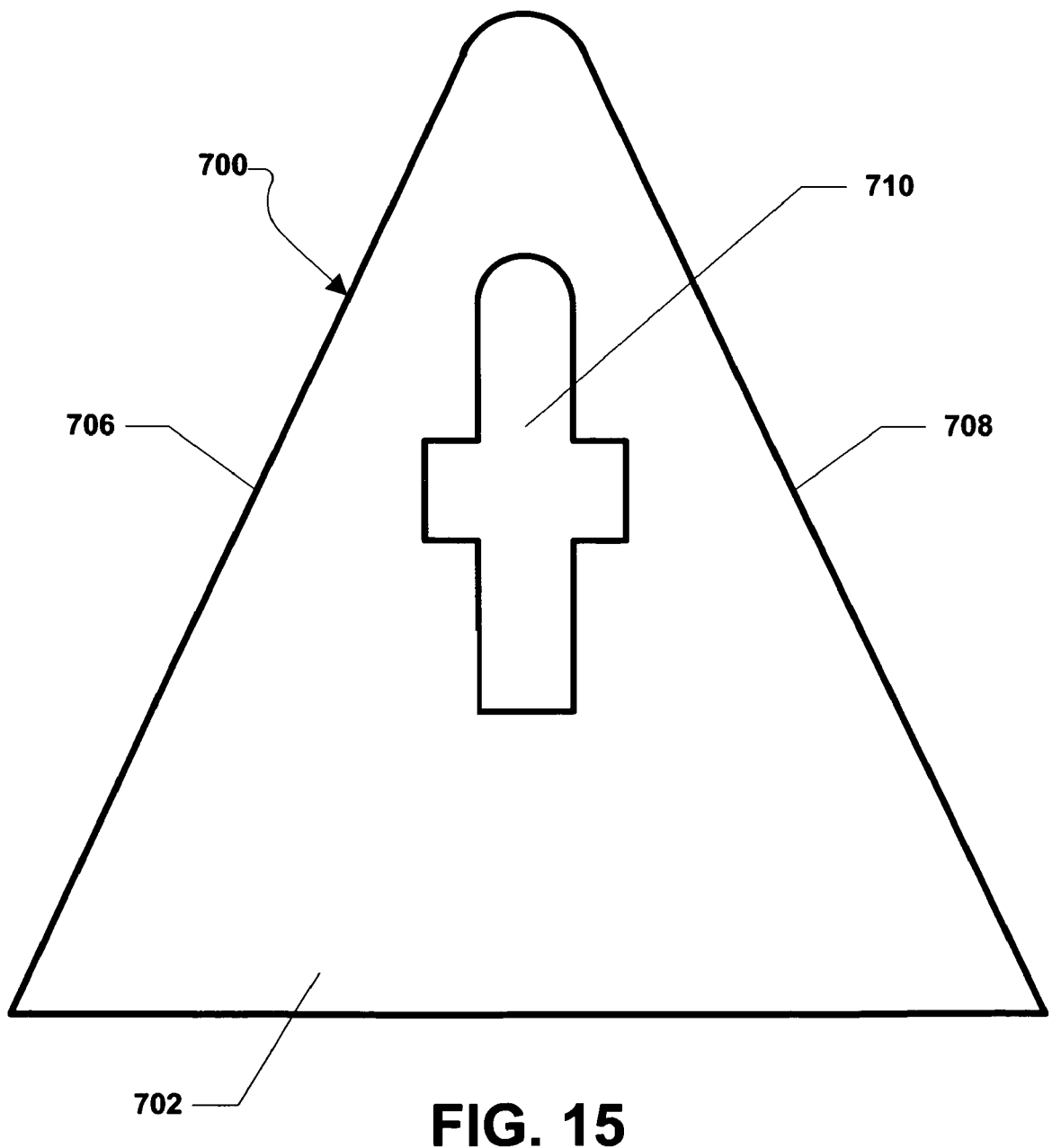
FIG. 15 is a top plan view of the bending wedge.
Figure 16:
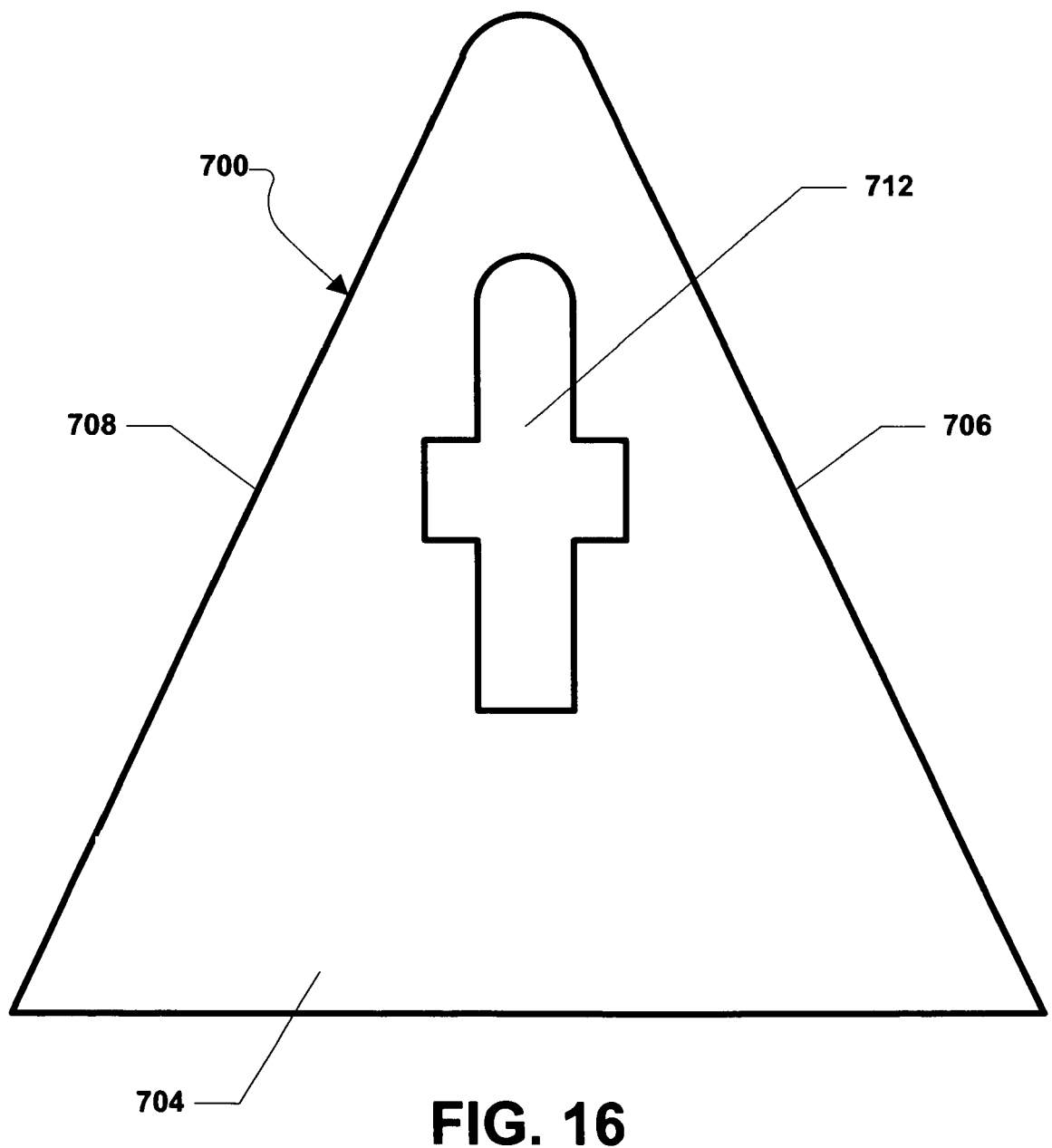
FIG. 16 is a bottom plan view of the bending wedge.

FIG. 14 through FIG. 16 illustrate details concerning the configuration of the bending wedge 700. As shown, the bending wedge 700 can include a superior surface 702 and an inferior surface 704. In a particular embodiment, the inferior surface 704 is substantially parallel to the superior surface 702. The bending wedge 700 can also include a first side surface 706 and a second side surface 708. In a particular embodiment, first side surface 706 is angled with respect to the second side surface 708 in order to establish the wedge shape of the bending wedge 700. The first side surface 706 and the second side surface 708 are substantially perpendicular to the superior surface 702 and the inferior surface 704 of the bending wedge 700.

As shown in FIG. 15, the superior surface 702 of the bending wedge 700 can include a superior opening 710. In a particular embodiment, the superior opening 710 can be generally cross-shaped and can be located along a longitudinal axis of the bending wedge 700. Alternatively, the superior opening 710 can be generally T-shaped. In a particular embodiment, the superior opening 710 is sized and shaped to fit over the superior bending wedge guide 230. More specifically, the superior opening 710 within the superior surface 702 can be configured to fit over the T-shaped cap 234 of the superior bending wedge guide 234. In a particular embodiment, when the bending wedge 700 is inserted over the superior bending wedge guide 230, the bending wedge 700 can slide along the post 232 of the superior bending wedge guide 230.

FIG. 16 indicates that the inferior surface 704 of the bending wedge 700 can include an inferior opening 712. In a particular embodiment, the inferior opening 712 can be generally cross-shaped and can be located along a longitudinal axis of the bending wedge 700. Alternatively, the inferior opening 712 can be generally T-shaped. In a particular embodiment, the inferior opening 712 is sized and shaped to fit over the inferior bending wedge guide 330. More specifically, the inferior opening 712 within the inferior surface 704 can be configured to fit over the T-shaped cap 334 of the inferior bending wedge guide 334. In a particular embodiment, when the bending wedge 700 is inserted over the inferior bending wedge guide 330, the bending wedge 700 can slide along the post 332 of the inferior bending wedge guide 330.

Description of the Operation of the Surgical Staple Assembly

Figure 17:
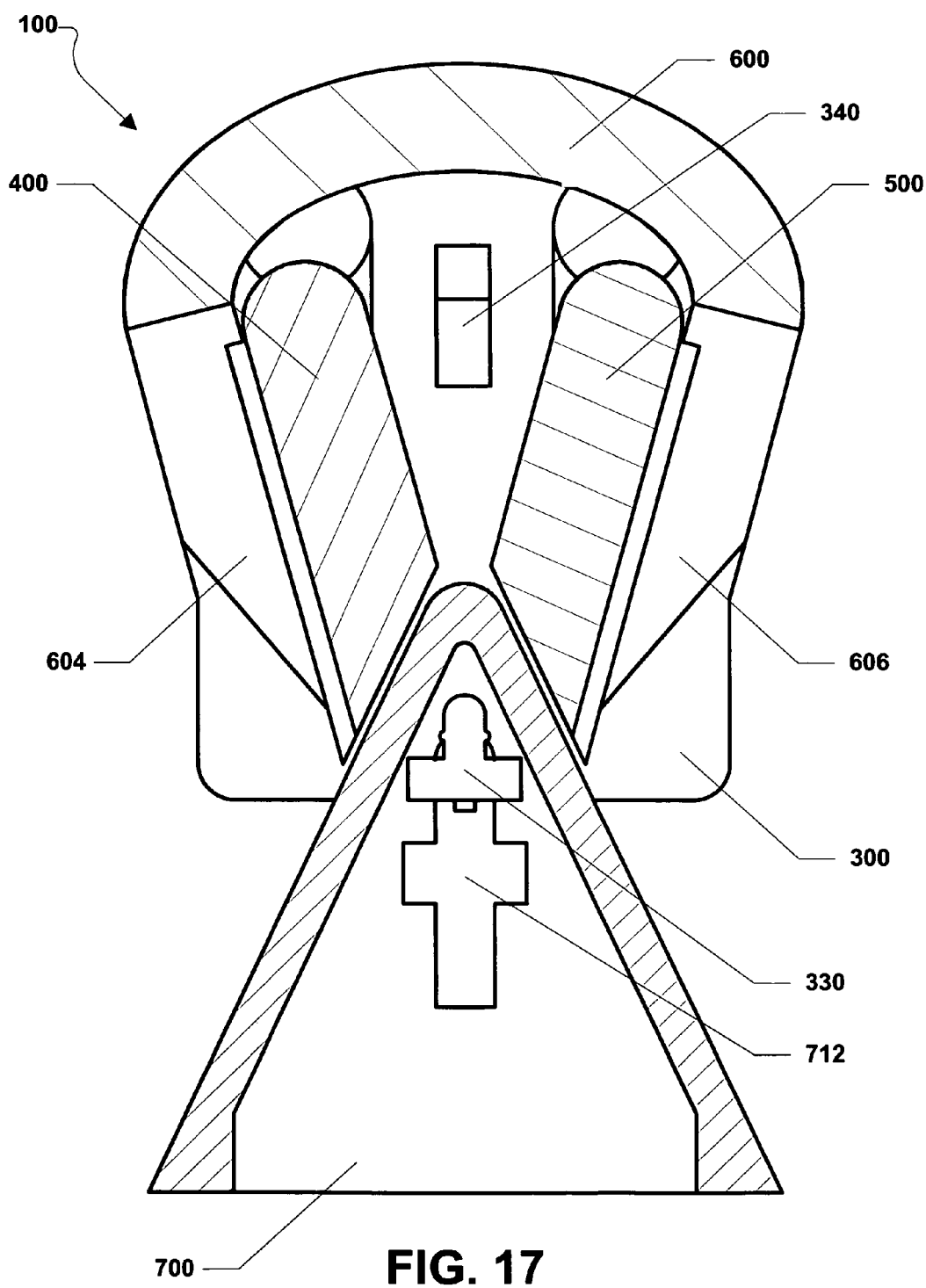
FIG. 17 is a cross section view of the surgical staple assembly in a first configuration.
Figure 18:
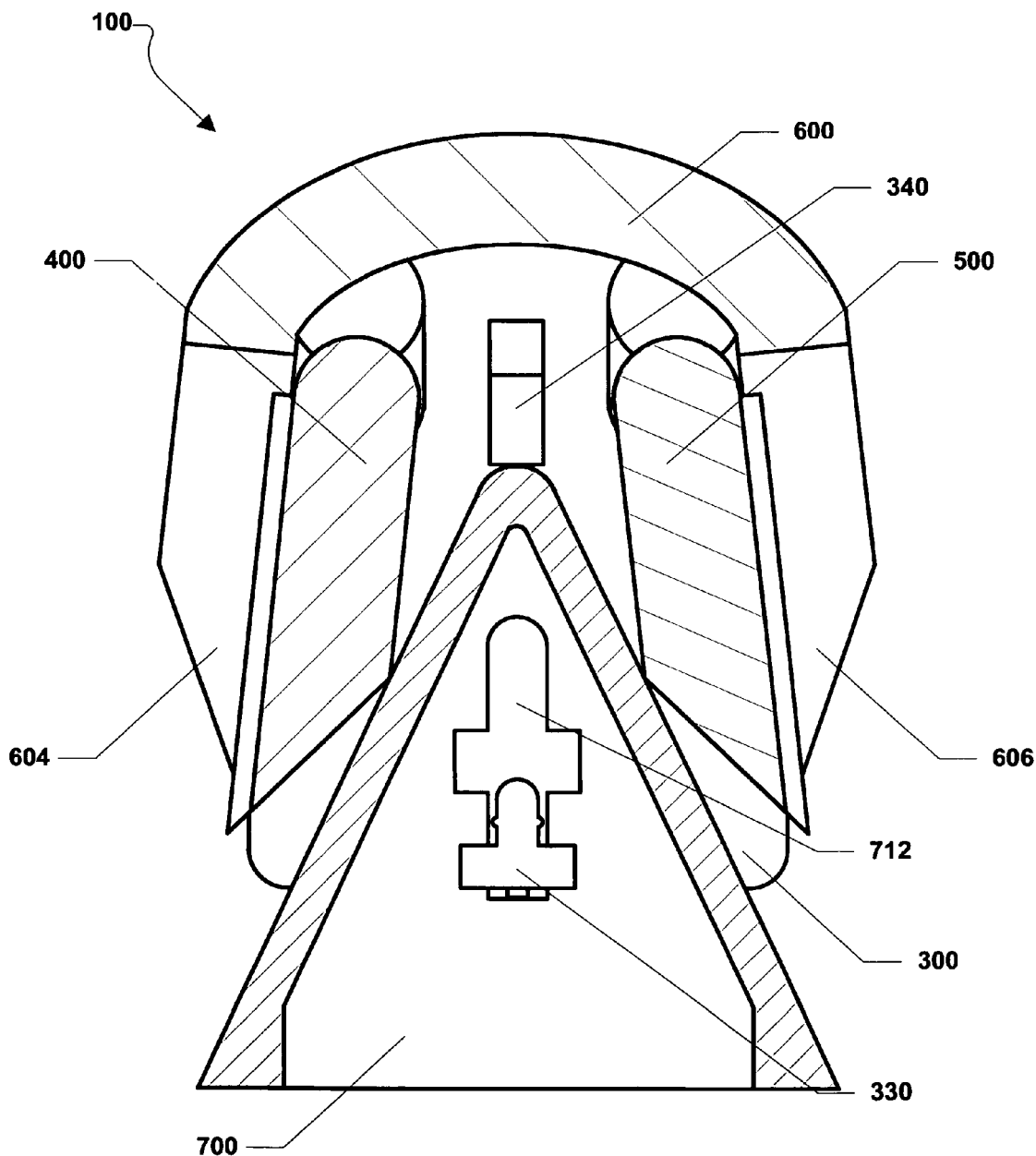
FIG. 18 is another cross-section view of the surgical staple assembly in a second configuration.

Referring now to FIG. 17 and FIG. 18, a cross-section of the surgical staple assembly 100 is shown. When the surgical staple is assembled, as shown in FIG. 17 and FIG. 18, the surgical staple 600 can be disposed around the bending arms 400, 500. Further, the bending wedge 700 can be placed at least partially between the bending arms 400, 500.

In a particular embodiment, the surgical staple assembly 100 is movable between a first configuration, shown in FIG. 17, in which the surgical staple 600 is in an original shape and a second configuration, shown in FIG. 18, in which the surgical staple 600 in a deformed configuration. In the deformed shape, the surgical staple 600 is opened, i.e., the tines 604, 606, 608, 610 are bent outward.

The surgical staple assembly 100 can be moved between the first configuration and the second configuration by sliding the bending wedge 700 relative to the superior support plate (not shown in FIG. 17 and FIG. 18) and the inferior support plate 300. As the bending wedge 700 slides into the surgical staple assembly 100, the bending wedge 700 can cause the bending arms 400, 500 to rotate outward. Moreover, as the bending arms 400, 500 rotate outward, the bending arms 400, 500 can bend the tines 604, 606, 608, 610. Specifically, the first bending arm 400 can bend the first superior tine 604 and the first inferior tine (not shown in FIG. 17 and FIG. 18) of the surgical staple 600. Further, the second bending arm 500 can bend the second superior tine 606 and the second inferior tine (not shown in FIG. 17 and FIG. 18).

The superior bending wedge stop (not shown in FIG. 17 and FIG. 18) and the inferior bending wedge stop 340 can limit the motion of the bending wedge 700. In other words, the superior bending wedge stop (not shown in FIG. 17 and FIG. 18) and the inferior bending wedge stop 340 can substantially prevent movement of the bending wedge 700 in the surgical staple assembly 100 beyond the wedge stops. As such, when multiple surgical staple assemblies are used, each surgical staple assembly 100 can be moved to the second configuration and the surgical staple 600 within each surgical staple assembly 100 can be bent to a consistent deformed configuration.

Description of a Set of Surgical Staple Assemblies

Figure 19:
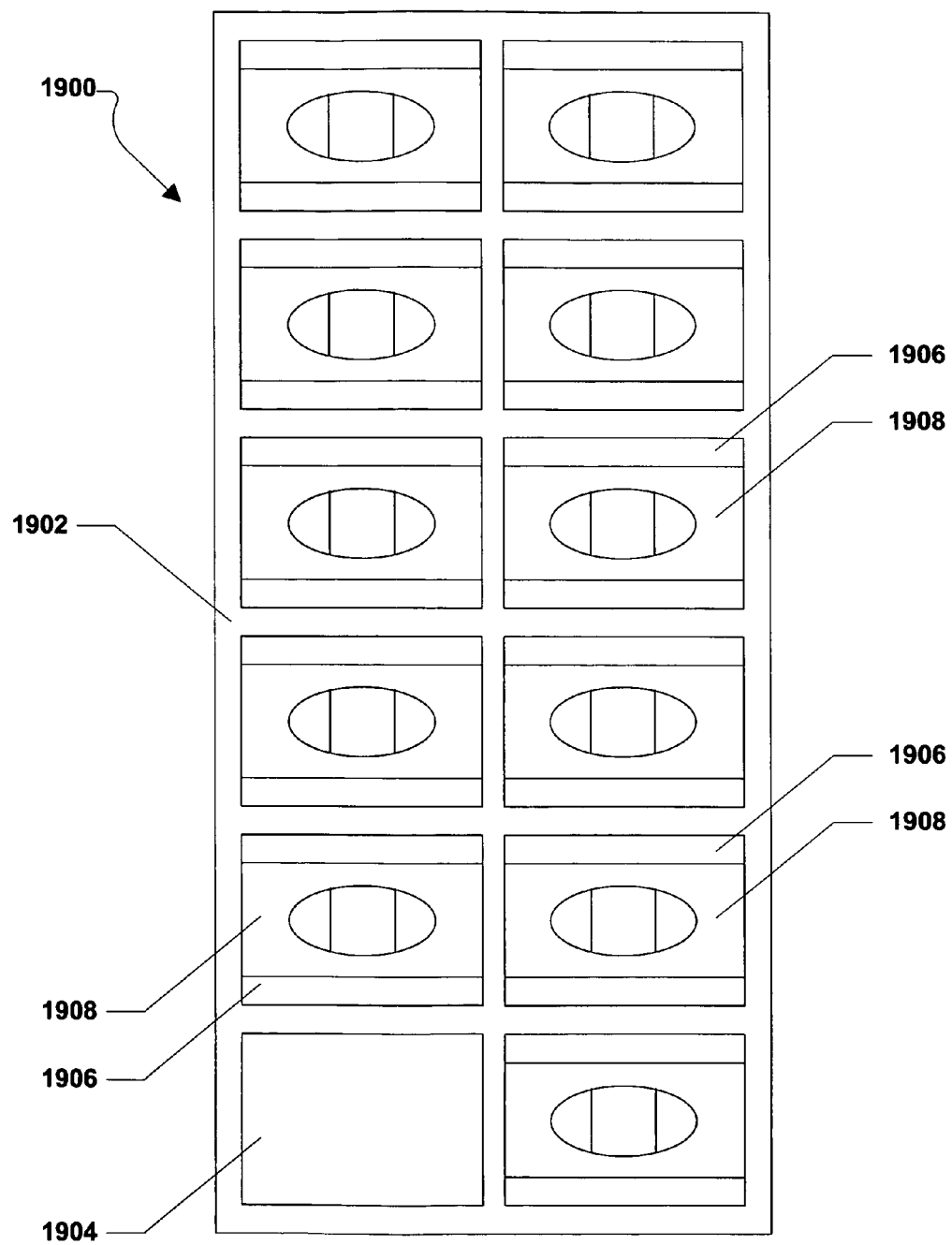
FIG. 19 is a plan view of a set of surgical staple assemblies.

FIG. 19 illustrates a set of surgical staple assemblies, generally designated 1900. As shown, the set of surgical staple assemblies 1900 can include a box 1902 that can have a plurality of openings 1904. Further, a surgical staple assembly 1906 can be placed within each opening 1904. In a particular embodiment, each surgical staple assembly 1906 can be a surgical staple assembly according to the present disclosure. Also, each surgical staple assembly 1906 can include a surgical staple 1908.

A surgical staple assembly 1906 can be retrieved from the box 1902 and moved to the second configuration, described above, in order to deform the surgical staple 1908. Thereafter, the surgical staple 1908 within the surgical staple assembly 1906 can be retrieved from the surgical staple assembly 1906 and inserted within a patient. As described above, each surgical staple 1908 can be bent to the same shape prior to insertion within the patient.

In a particular embodiment, the set of surgical staple assemblies 1900 can include four-tine surgical staples, two-tine surgical staples, or a combination thereof. Further, the set of surgical staple assemblies 1900 can include surgical staples having various sizes and the different sized staple assemblies can be color coded by size.

Description of a Method of Using a Surgical Staple Assembly

Figure 20:
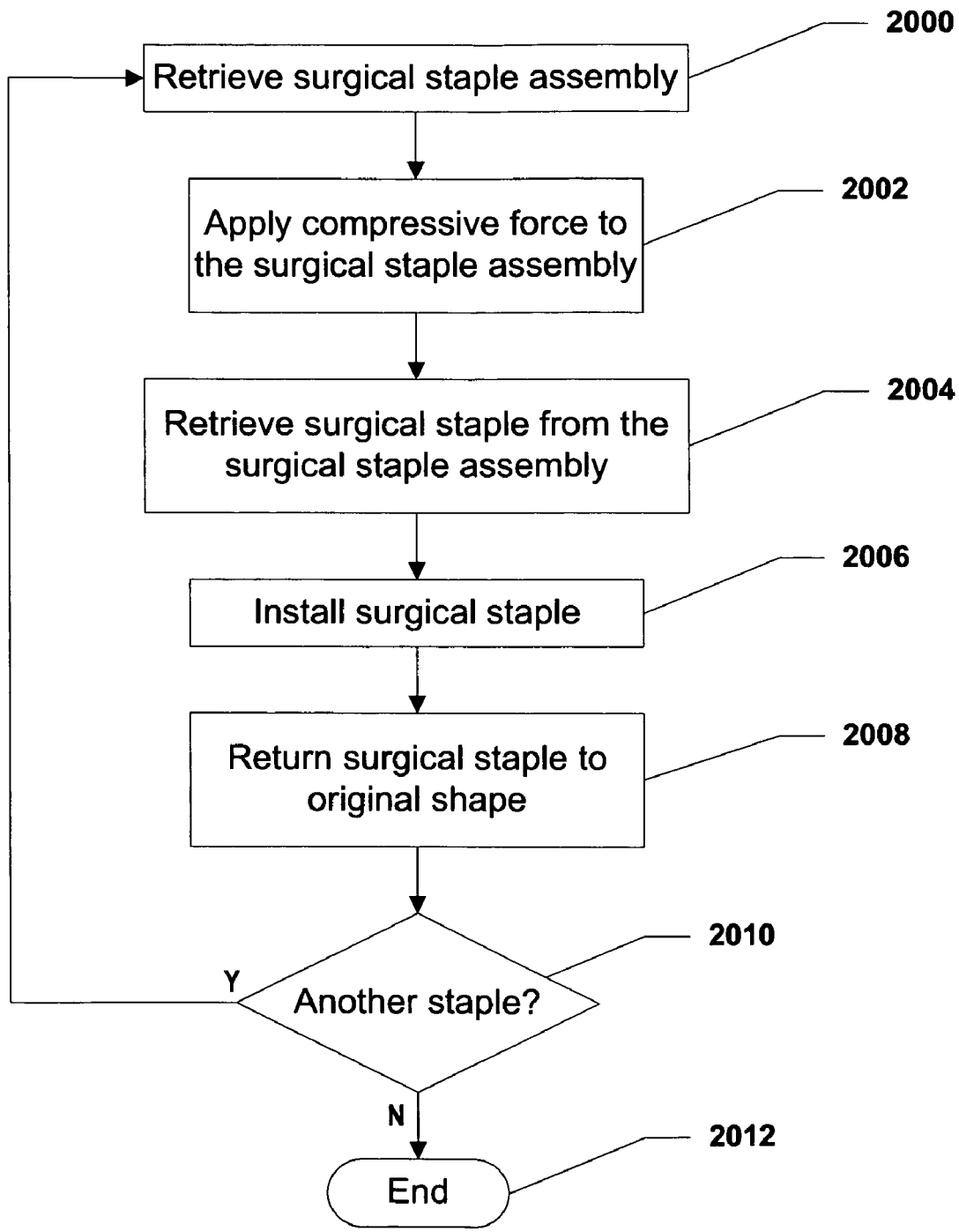
FIG. 20 is a flow chart illustrating one method of using a surgical staple assembly.

Referring to FIG. 20, a method of using a surgical staple assembly is shown. In a particular embodiment, the surgical staple assembly is the surgical staple assembly shown and described herein. Commencing at block 2000, a surgical staple assembly can be retrieved. At block 2002, a compressive force can be applied to the surgical staple assembly. In a particular embodiment, the compressive force can drive a wedge of the surgical staple assembly into the surgical staple assembly. The wedge can bend the tines of a surgical staple within the surgical staple assembly. More specifically, the tines of the surgical staple can be bent outward.

Moving to block 2004, the surgical staple can be retrieved from the surgical staple assembly. Further, at block 2006, the surgical staple can be installed. For example, the surgical staple can be installed in a patient, e.g., in a bone of the patient or in a fleshy or meaty part of the patient. At block 2008, the surgical staple can be returned to the original shape of the surgical staple, e.g., the shape of the surgical staple before application of the compressive force to the surgical staple assembly. In a particular embodiment, the surgical staple can be made from a memory metal alloy and the surgical staple can be returned to the original shape by applying heat to the surgical staple.

Continuing to decision step 2010, it can be determined whether another surgical staple is required, e.g., by a doctor or surgeon. If another surgical staple is required, the method can return to block 2000 and continue as described herein. On the other hand, if another surgical staple is not required, the method can end at state 2012.

Description of an Alternative Embodiment of a Surgical Staple

Figure 21:
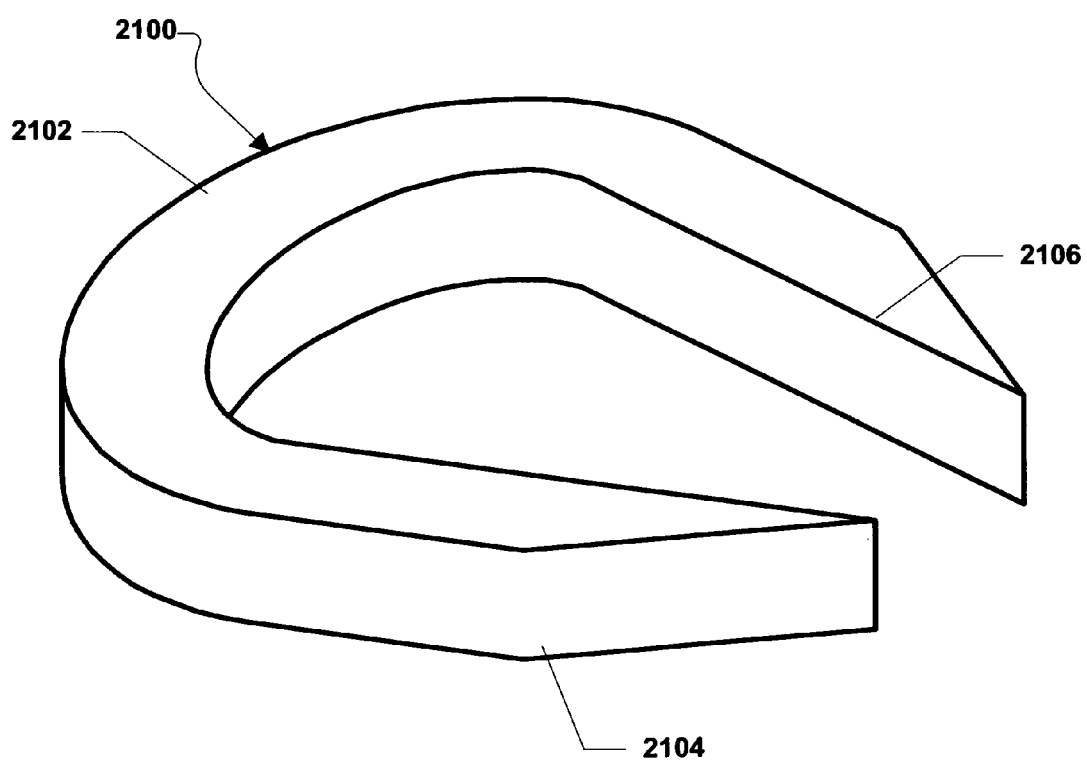
FIG. 21 is a perspective view of an alternative embodiment of a surgical staple.
Figure 22:
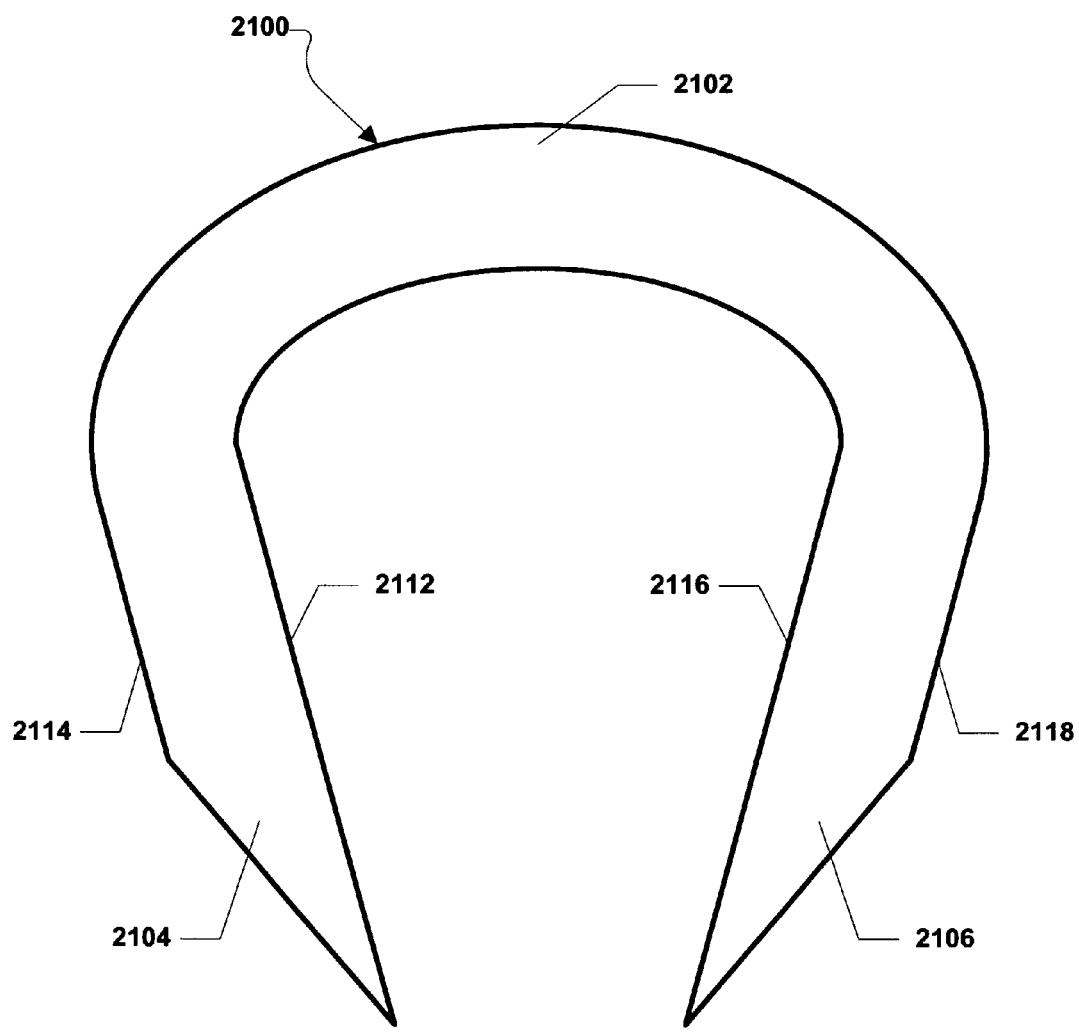
FIG. 22 is a plan view of the alternative embodiment of the surgical staple.

Referring to FIGS. 21 and 22, an alternative embodiment of a surgical staple is shown and is generally designated 2100. As shown, the surgical staple 2100 can include a base 2102. A first tine 2104 and a second tine 2106 can extend from the base 2102.

As shown in FIG. 22, the first tine 2104 can include an inner surface 2112 and an outer surface 2114. The second tine 2106 can also include an inner surface 2116 and an outer surface 2118.

Figure 23:
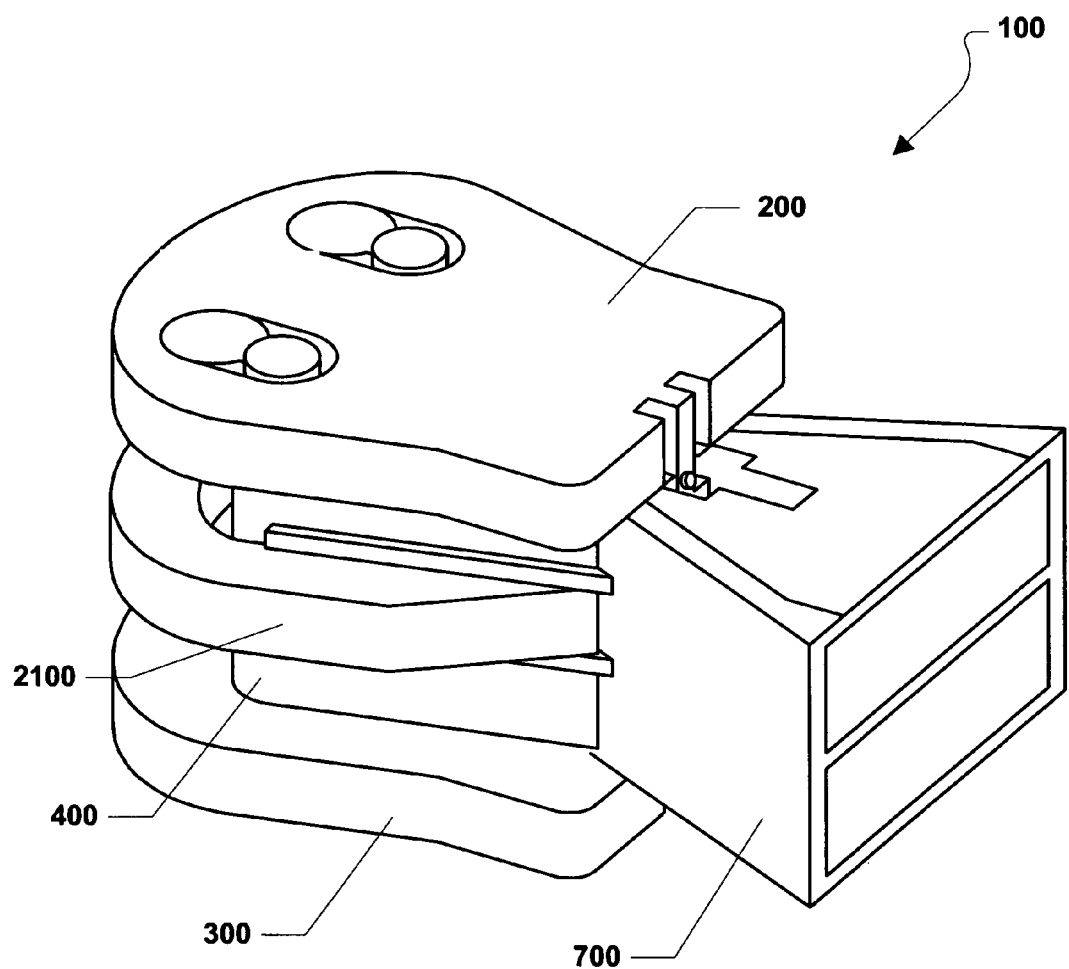
FIG. 23 is a perspective view of a surgical staple assembly including the alternative embodiment of the surgical staple.

In a particular embodiment, the four-tine surgical staple 600, described above, can be removed from the surgical staple assembly 100 and replaced with the two-tine surgical staple 2100. As shown in FIG. 23, the two-tine surgical staple 2000 can be disposed around the bending arms 400, 500 between the ribs 430, 432, 530, 532 on each bending arm 400, 500.

Specifically, the inner surface 2112 of the first tine 2104 can be adjacent to the outer surface 408 of the first bending arm 400. Also, the inner surface 2116 of the second tine 2106 can be adjacent to the outer surface 508 of the second bending arm 400. Moreover, the first tine 2104 can be disposed between the ribs 430, 432 of the first bending arm 400 and the ribs 430, 432 can engage and support the first tine 2104 along the first bending arm 400. The second tine 2106 can be disposed between the ribs 530, 532 of the second bending arm 500 and the ribs 530, 532 can engage and support the second tine 2106 along the second bending arm 500.

Accordingly, as the bending arms 400, 500 are pushed outward by the bending wedge 700, as described herein, the bending arms 400, 500 can bend the tines 2104, 2106 of the surgical staple 2100. More specifically, as the first bending arm 400 is pushed outward, the first bending arm 400 can bend the first tine 2104 of the surgical staple 2100. Moreover, as the second bending arm 500 is pushed outward, the second bending arm 500 can bend the second tine 2106 of the surgical staple 2100.

CONCLUSION

With the configuration of structure described above, the surgical staple assembly provides a device that can be used to bend a surgical staple to a deformed configuration prior to installation in a patient. Further, the surgical staple assembly can be used to consistently bend a staple to the same shape. When multiple surgical staple assemblies are used, each surgical staple within each surgical staple assembly can be bent to the same shape.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A surgical staple assembly, comprising:
a superior support plate;
an inferior support plate spaced from the superior support plate;
a surgical staple configured to be placed between the superior support plate and the inferior support plate, wherein the surgical staple assembly is movable between a first configuration wherein the surgical staple is in an original shape and a second configuration wherein the surgical staple is in a deformed configuration, the surgical staple having at least two tines;
a first bending arm configured to be disposed and to rotate between the superior support plate and the inferior support plate to deform the surgical staple; and
a second bending arm configured to be disposed and to rotate between the superior support plate and the inferior support plate to deform the surgical staple, and the first bending arm and the second bending arm are disposed between at least two of the tines and to force apart said at least two tines;
a bending wedge between interiors of the first bending arm and the second bending arm to force apart the bending arms from each other; and the superior support plate further comprises:
a superior bending wedge guide configured to engage the bending wedge and guide the bending wedge as the bending wedge moves within the surgical staple.

2. The surgical staple assembly of claim 1, wherein the bending wedge is configured to be moved into the surgical staple.

3. The surgical staple assembly of claim 2, wherein the first bending arm and the second bending arm rotate outward as the bending wedge is moved into the surgical staple.

4. The surgical staple assembly of claim 3, wherein the surgical staple is deformed as the bending wedge is moved into the surgical staple.

5. The surgical staple assembly of claim 1, wherein the superior support plate further comprises:
a superior bending wedge stop configured to limit the motion of the bending wedge as the bending wedge moves within the surgical staple.

6. The surgical staple assembly of claim 5, wherein the inferior support plate further comprises:
an inferior bending wedge guide configured to engage the bending wedge and guide the bending wedge as the bending wedge moves within the surgical staple.

7. The surgical staple assembly of claim 6, wherein the inferior support plate further comprises:
an inferior bending wedge stop configured to limit the motion of the bending wedge as the bending wedge moves within the surgical staple.

8. The surgical staple assembly of claim 1, wherein the superior bending wedge guide comprises a protrusion and wherein the superior bending wedge guide is configured to produce a clicking noise when the protrusion is contacted.

9. The surgical staple assembly of claim 8, wherein the protrusion is configured to be contacted by the bending wedge.

10. The surgical staple assembly of claim 6, wherein the inferior bending wedge guide comprises a protrusion and wherein the inferior bending wedge guide is configured to produce a clicking noise when the protrusion is contacted.

11. The surgical staple assembly of claim 10, wherein the protrusion is configured to be contacted by the bending wedge.

12. A surgical staple assembly, comprising:
a surgical staple, wherein the surgical staple assembly is movable between a first configuration wherein the surgical staple is in an original shape and a second configuration wherein the surgical staple is in a deformed configuration;
a first bending arm;
a second bending arm, wherein the first bending arm and the second bending arm are movable to deform the surgical staple;
a bending wedge configured to be placed between and contact interiors of the first bending arm and the second bending arm to force them apart, the bending wedge being configured to be moved into an interior of the surgical staple;
the first bending arm and the second bending arm rotate outward as the bending wedge is moved into the surgical staple to spread apart the surgical staple;
a superior support plate;
an inferior support plate distanced from the superior support plate, wherein the first bending arm and the second bending arm are rotatably disposed between the superior support plate and the inferior support plate;
the superior support plate is formed with a first hole and a second hole and wherein the inferior support plate is formed with a first hole and a second hole; and
the first bending arm comprises: a superior post configured to engage the first hole within the superior support plate; and an inferior post configured to engage the first hole within the inferior support plate.

13. The surgical staple assembly of claim 12, wherein the first bending arm and the second bending arm are disposed proximate to the surgical staple and wherein the first bending arm and the second bending arm are configured to bend the staple outward.

14. The surgical staple assembly of claim 13, wherein the surgical staple comprises:
a first superior tine;
a second superior tine opposite the first superior tine;
a first inferior tine opposite the first superior tine; and
a second inferior tine opposite the first inferior tine.

15. The surgical staple assembly of claim 14, wherein the first bending arm and the second bending arm are disposed between the first superior tine, the first inferior tine, the second superior tine, and the second inferior tine.

16. The surgical staple assembly of claim 15, wherein the first bending arm is configured to bend the first superior tine and the first inferior tine.

17. The surgical staple assembly of claim 16, wherein the first bending arm is configured to bend the first superior tine and the first inferior tine outward.

18. The surgical staple assembly of claim 15, wherein the second bending arm is configured to bend the second superior tine and the second inferior tine.

19. The surgical staple assembly of claim 18, wherein the second bending arm is configured to bend the second superior tine and the second inferior tine outward.

20. The surgical staple assembly of claim 13, wherein the surgical staple comprises:
a first tine; and
a second tine opposite the first tine.

21. The surgical staple assembly of claim 20, wherein the first bending arm and the second bending arm are disposed between the first tine, and the second tine.

22. The surgical staple assembly of claim 21, wherein the first bending arm is configured to bend the first tine.

23. The surgical staple assembly of claim 22, wherein the first bending arm is configured to bend the first tine outward.

24. The surgical staple assembly of claim 22, wherein the second bending arm is configured to bend the second superior tine and the second inferior tine.

25. The surgical staple assembly of claim 24, wherein the second bending arm is configured to bend the second tine outward.

26. The surgical staple assembly of claim 20, wherein the first bending arm comprises a rib configured to support the first tine.

27. The surgical staple assembly of claim 26, wherein the second bending arm comprises a rib configured to support the second tine.

28. The surgical staple assembly of claim 12, wherein the second bending arm comprises:

a superior post configured to engage the second hole within the superior support plate; and an inferior post configured to engage the second hole within the inferior support plate.

29. The surgical staple assembly of claim 12, wherein the surgical staple is deformed as the bending wedge is moved into the surgical staple.

* * * * *